(12) United States Patent
Nikolskaya et al.

(10) Patent No.: US 8,010,331 B2
(45) Date of Patent: Aug. 30, 2011

(54) SYSTEM RECONSTRUCTION: INTEGRATIVE ANALYSIS OF BIOLOGICAL DATA

(75) Inventors: Tatiana Nikolskaya, Portage, IN (US); Andrej Bugrim, St. Joseph, MO (US); Aleksander Markov, Moscow (RU); Evgeny Kirtlov, Moscow (RU); Igor Gariev, Pushching (RU)

(73) Assignee: Genego, Inc., Encinitas, CA (US)

( * ) Notice: Subject to any disclaimer, the term of this patent is extended or adjusted under 35 U.S.C. 154(b) by 1473 days.

(21) Appl. No.: 10/174,762

(22) Filed: Jun. 18, 2002

(65) Prior Publication Data

US 2006/0235624 A1    Oct. 19, 2006

Related U.S. Application Data

(60) Provisional application No. 60/299,040, filed on Jun. 18, 2001.

(51) Int. Cl.
*G06G 7/58* (2006.01)
(52) U.S. Cl. ......... 703/11
(58) Field of Classification Search .......... None
See application file for complete search history.

(56) References Cited

U.S. PATENT DOCUMENTS

| | | | |
|---|---|---|---|
| 6,074,616 A * | 6/2000 | Buechler et al. | 422/104 |
| 2002/0198858 A1 * | 12/2002 | Stanley et al. | 706/50 |
| 2003/0233218 A1 * | 12/2003 | Schilling | 703/11 |

FOREIGN PATENT DOCUMENTS

WO    WO -01/13105    2/2001

OTHER PUBLICATIONS

Nakao et al. (Genome scale gene expression analysis and pathway reconstruction in KEGG, Genome Informatics, 10:94-103, 1999).*
Okubo et al. (Nature Genetics, vol. 2, p. 173-179, Nov. 1992).*
Karp et al. (Trends in biotechnology, vol. 17, p. 275-281, 1999).*
Ochs et al. (J. Chem. Inf. Comput. Sci., vol. 36, No. 3, p. 594-601, 1996).*
Ishizuka et al. (Information processing society of Japan, vol. 91, p. 73-80, Sep. 27, 2000).*
Takai-Igarashi et al. (In Silico Biology, vol. 1, p. 129-146, 1999).*
Forst et al. (Journal of Computational Biology vol. 6, Nos. 3/4, 1999, pp. 343-360).*
Van Heyningen (Molecular Medicine, vol. 3, No. 4, Apr. 1997. 231-237).*
Juty et al. (Briefings in Bioinformatics, vol. 2. No. 3, p. 223-232, Sep. 2001).*
Adams et al., Curr Opin Microbiol (1998) 1(6):674-677.
Adams et al., Microbiol Mol Biol Rev (1998) 62(1):35-54.
Brakhage, Microbiol Mol Biol Rev (1998) 62(3):547-585.
Selkov et al., Gene (1997) 197:GC11-GC26.
Venter et al., Science (2001) 291:1304-1351.
Bairoch and Apweiler, Nucleic Acids Res (2000) 28:45-48.
Guzman-De-Pena et al., Antonie Van Leeuwenhoek (1998) 73(2):199-205.
Kanehisha et al., Nucleic Acids Res (2002) 30:42-46.
Karp et al., Nucleic Acids Res Res (2002) 30:56-58.
Overbeek et al., Nucleic Acids Res (2000) 28(1):123-125.
Schomburg et al., Nucleic Acids Res (2002) 30:47-49.
Selkov et al., Nucleic Acids Res (1998) 26:43-45.

* cited by examiner

*Primary Examiner* — Karlheinz R Skowronek
(74) *Attorney, Agent, or Firm* — Morrison & Foerster LLP

(57) ABSTRACT

The process of System Reconstruction is used to integrate sequence data, clinical data, experimental data, and literature into functional models of disease pathways. System Reconstruction models serve as informational "skeletons" for integrating various types of "high throughput" data. The present invention provides the first metabolic reconstruction study of a eukaryotic organism based solely on expressed sequence tag (EST) data.

17 Claims, 54 Drawing Sheets

Example of an enzyme page: Methionine adenosyltransferase
EC 2.5.1.6 Methionine adenosyltransferase

| Names |
|---|
| Adenosylmethionine synthetase |
| Adenosyltransferase, methionine |
| AdoMet synthetase |
| ATP:L-methionine S-adenosyltransferase |
| ATP:L-methionine-S-adenosyltransferase |
| ATP-methionine adenosyltransferase |
| EC 2.4.2.13 (formerly) |
| Methionine adenosyltransferase |
| Methionine S-adenosyltransferase |
| Methionine-activating enzyme |
| S-Adenosyl-L-methionine synthetase |
| S-Adenosylmethionine synthase |
| S-Adenosylmethionine synthetase |

Human genes assigned:

| Symbol | Name | SwissProt | UniGene |
|---|---|---|---|
| MAT1A | methionine adenosyltransferase I, alpha | Q00266 | Hs.323715 |
| MAT2A | methionine adenosyltransferase II, alpha (catalytic) | P31153 | Hs.77502 |
| MAT2B | methionine adenosyltransferase II, beta (non-catalytic) | = | Hs.54642 |

NEXT >

FIG. 9A

Methionine adenosyltransferase page, continued
EC 2.5.1.6 Methionine adenosyltransferase

Names

Adenosylmethionine synthetase
Adenosyltransferase, methionine

Human genes assigned:

| Symbol | Name | SwissProt | UniGene |
|---|---|---|---|
| MAT1A | methionine adenosyltransferase I, alpha | Q00266 | Hs.323715 |
| MAT2A | methionine adenosyltransferase II, alpha (catalytic) | P31153 | Hs.77502 |
| MAT2B | methionine adenosyltransferase II, beta (non-catalytic) | = | Hs.54642 |

*Click on gene symbols to view gene pages*

Pathways & Reactions

Reactions (Cytosol) L-methionine + $H_2O$ + ATP = 'S' adenosyl-1-L-methionine + phosphate + pyrophosphate

*Click here to view reaction page*

Pathways

L-methionine/L-serine//pyrophosphate/2-oxobutanoate/adenosine/L-cysteine//cyt

Annotations

1

| Diseases | hypermethioninemia (methionine adenosyltransferase deficiency), cancer, carcinoma |
|---|---|
| Note | |
| PMID | 11145114, 2345265, 6871179, 10921051, 10955733, 10677294 |
| Tissue/Cells | Plasma, Kidney, Erythrocytes, Chronic lymphocytic leukemia cells, Liver, Breast cancer cell lines, Colon, N/A |

NEXT >

FIG. 9B

Reaction page

(Cytosol) L-methionine + $H_2O$ + ATP = 'S' adenosyl-L-methionine + phosphate + pyrophosphate

| Location | Cytosol |
|---|---|
| Catalyst | 2.5.1.6 |
| Cefs | |
| Revers | No |

| Chem | StC | CoenzType |
|---|---|---|
| pyrophosphate | -1 | |
| ATP | 1 | |
| H(,2)O | 1 | donor |
| L-methionine | 1 | |
| phosphate | -1 | |
| 'S'-adenosyl-L-methionine | -1 | |

Annotations

1

| Diseases | hypermethioninemia (methionine adenosyltransferase deficiency) |
|---|---|
| Note | |
| PMID | 6871179,11145114,2345265 |
| Tissue/Cells | Erythrocytes,Kidney |

2

| Diseases | cirrhosis |
|---|---|
| Note | Catalytically active human and rat liver S-adenosylmethionine synthetase exists mainly in tetramer and dim form. In liver biopsy samples from cirrhotic patients a marked reduction in total S-adenosylmethionine synthetase activity and a specific loss of the tetrameric form of the enzyme exist. Because treatment of S-adenosylmethionine synthetase with N-ethylmaleimide resembles the situation of this enzyme in cirrhotic patients, it is proposed that impaired protection of the enzyme from oxidizing agents caused by a decreased synthesis of glutathione can explain the diminished synthesis of S-adenosylmethionine in liver cirrhosis. |
| PMID | 2307400 |
| Tissue/Cells | Liver |

FIG. 10

Gene page
Gene MAT2A

| | |
|---|---|
| Symbols | MAT2A SAMS2 MAT II |
| Location | 02 p11.2 |
| Names | methionine adenosyltransferase II, alpha (catalytic)<br>S-adenosylmethionine synthetase 2,gamma(non-hepatic or kidney-specific) |
| OMIM | 601468 |
| Enzyme | 2.5.1.6 |
| GDB | 136213 |
| SwissProt | P31153 |
| UniGene | Hs.77502 |
| Sequences | BC001686 BC001854 X68836 |

Expressed in
adrenal gland; amnion_normal; b-cells; bladder; blood; bone; bone marrow; brain; breast; breast_normal; cervix; cns; colon; colon_ins; colon_normal; connective tissue; denis drash; ear; epid_tumor; esophagus; eye; foreskin; germ cell; head_neck; head_normal; heart; kidney; leiomios; liver; lung; lymph; marrow; muscle; nervous_normal; nervous_tumor; ovary; pancreas; parathyroid; placenta; pool; prostate; prostate_normal; prostate_tumor; skin; skin_normal, 4 pooled samples; small intestine; stomach; stomach_normal;testis; testis; cell line; tonsil; uterus; uterus_tumor; whole embryo

Amino Acid Sequence
INGQLNGFHEAFIEEGTFLFTSESVGEGHPDKICDQISDAVLDAHLQQDPDAKVACETVAKTGMILLAGEITSRAAVDYQKVVREA\

Number of ESTs from different organs/tissues (fetal ESTs and those without explicit organ/tissue data are excluded)

| Liver | Brain | Kidney | Heart | Lung | Total |
|---|---|---|---|---|---|
| 2 | 35 | 30 | 14 | 52 | 445 |
| 0% | 7% | 6% | 3% | 11% | 100% |

FIG. 11

| Compound page | |
|---|---|
| S-adenosyl-L-methionine | |

Annotations

1

| | |
|---|---|
| Diseases | |
| Diseases note | |
| Note | S-adenosyl-L-methionine (SAMe); a molecule naturally present in several body tissues and fluids, is produced, by SAMe synthetase, from ATP and methionine. SAMe has a fundamental role, as methyl group donor, in transmethylation reactions in which the synthesis of membrane phospholipids is mandatory for the maintenance of membrane fluidity. Another metabolic pathway involving SAMe, transsulphuration, is initiated with the release of -CH3 from the molecule and the formation of S-Adenosyl-homocysteine and then homocysteine and cysteine, a precursor of glutelhione the main cellular antioxident, responsible of detoxification of various compounds and xenobiotics. |
| PMID | 1299337 |
| Tissue/Cells | liver |

FIG. 12

Parkinson disease page

Annotations

1

| Diseases | Parkinson disease, Parkinson disease, association with, idiopathic parkinsonism. |
|---|---|
| Note | |
| PMID | 1683212, 8988461, 10619718, 309860, 11056194, 8825899, 34555, 3540926, 8965384, 10643794, 6441736, 1041: |

2

| Diseases | Parkinson disease |
|---|---|
| Note | The increase in platelet MAO-B activity and decrease in plasma PEA concentrations in patients with Parkinson's disease may be involved in the pathophysiological processes of the disease, and these changes are reversed by treatment with selegiline. |
| PMID | 11160474 |

3

| Diseases | Parkinson disease |
|---|---|
| Note | AAAD is the second enzyme in the sequence leading to the synthesis of the catecholamines and serotonin, and it is the rate-limiting enzyme for the synthesis of the trace amines. In the striatum AAAD activity is increased by nemonal firing and diminished or enhanced by activation or blocking dopamine (DA) D1 or D2 receptors, respectively. A1 least two biochemical mechanisms appear responsible for modulation, short-term involving second messengers and possible phosphorylation, and long-term involving protein synthesis. In Parkinson's disease AAAD is the rate-controlling enzyme for the synthesis of DA when L-DOPA is administered and any change of AAAD activity could have clinical consequences. |
| PMID | 8584678 |

FIG. 17

3-phospho-D-glycerate/L-glutamate//2-oxoglutarate/L-serine//c\
View ▶ scheme

Reactions
| | |
|---|---|
| 1.1.1.95 | (Cytosol) 3-phospho-D-glycerate + NAD$^+$ = 3-phosphohydroxypyruvate + NADH |
| 2.6.1.52 | (Cytosol) 3-phosphohydroxypyruvate + L-glutamate = 'O'-phospho-L-serine + 2-oxoglutarate |
| 3.1.3.3 | (Cytosol) 'O'-phospho-L-serine + H$_2$O = L-serine + phosphate |

Enzymes

| EC number | Genes | Expressed in | ESTs |
|---|---|---|---|
| 1.1.1.95 | PHGDH | adrenal gland; aorta; b-cells; bladder; blood; bocio_tumor; bone; bone marrow; brain; breast; breast_normal; cervix; cns; colon; colon_est; colon_ins; colon_normal; esophagus; eye; fetal brain; foreskin; germ cell; head_neck; heart; kidney; kidney_tumor; liver; lung; lung_tumor; lymph; marrow; muscle; muscle (skeletal); nervous_normal; nervous_tumor; nose; ovary; pancreas; parathyroid; placenta; placenta_normal; pnet; pool; pooled; pooled colon, kidney, stomach; pooled pancreas and spleen; prostate; prostate_normal; skin; small intestine; synovial membrane; testis; testis, cell line; thymus, pooled; tissue culture; tonsil; uterus; uterus_tumor; whole embryo | AA021612 AA046094 AA09 AA093706 AA093721 AA10 AA101560 AA113268 AA11 AA114165 AA114201 AA12( AA129452 AA134085 AA13 AA137039 AA143014 AA14: AA146617 AA147630 ...(tot: 1145) |
| 2.6.1.52 | PSA | adrenal gland; aorta; blood; bone; bone marrow; brain; breast; cervix; cns; colon; colon_est; colon_ins; colon_normal; denis_drash; ear; eye; fetal brain; foreskin; genitourinary tract; germ cell; head_neck; heart; kidney; leiomios; lung; lung, cell line; lymph; muscle; nervous_tumor; normal head/neck tissue; ovary; pancreas; placenta; placenta_normal; pool; pooled; prostate; skin; spleen; stomach; testis; testis, cell line; testis_normal; thymus, pooled; tonsil; uterus; whole embryo | AA025924 AA057399 AA07! AA084923 AA085026 AA12" AA134792 AA137152 AA17: AA173918 AA178173 AA18" AA192412 AA192483 AA19! AA224438 AA224501 AA25; AA307911 AA315484 ...(tota 467) |
| 3.1.3.3 | PSPH | adrenal gland; aorta; bone; bone marrow; brain; cervix; colon; colon_est; eye; kidney; liver; lung; muscle (skeletal); nervous_tumor; pancreas; placenta; pool; pooled lung and spleen; prostate; stomach; thyroid; whole embryo | AA488432 AA488571 AA621 AI370893 AI479788 AL5251! AL526979 AL527020 AL528( AL529170 AL562450 AL563( AL563371 AU118817 AU124 AU143638 AU148622 AU160327 AU160699 AW029526 ...(total 89) |

Annotations
1

Diseases: carcinoma, Fanconi anemia, Williams-Beuren syndrome (WS; WBS; MIM:194050), Alzheimer disease (MIM:104300)

Note

PMID

2
Diseases 3-phosphoglycerate dehydrogenase deficiency
Note 3-Phosphoglycerate dehydrogenase (3-PGDH) deficiency is an inborn error of serine biosynthesis. Patients are affected with congenital microcephaly, psychomotor retardation, and intractable seizures. The effects of oral treatment with amino acids were investigated in 2 siblings. L-Serine up to 500 mg/kg/day was not sufficient for seizure control. Addition of glycine 200 mg/kg/day resulted in complete disappearance of seizures. Electroencephalographic abnormalities gradually resolved after 6 months. We conclude that 3-PGDH can be treated effectively by a combination of L-serine and glycine.
PMID 8758134, 9708551

3
Diseases
Note In particular in tissues with a high rate of cell turnover, phosphoserine aminotransferase and serine hydroxymethyltransferase activities were coordinately increased (6089514).
PMID 6089514

4
Diseases cancer susceptibility, prostate and brain, carcinoma, leukemia, lymphoma
Note The nucleotide sequence of Hs 3-PGDH gene, encoding human 3-phosphoglycerate dehydrogenase that catalyzes the initiating step in the phosphorylated pathway of serine biosynthesis, has been determined. The 3-PGDH gene has a predicted 533 amino acid open reading frame, encoding a 56.8kDa protein that shares 94.0% similarity with rat-liver 3-PGDH. Two different transcripts corresponding to 3-PGDH mRNA were detected in human normal tissues. A dominant 2.1kb transcript was expressed at high levels in prostate, testis, ovary, brain, liver, kidney, and pancreas, and weakly expressed in thymus, colon, and heart. A 710bp transcript also appeared as a weaker band where the 2.1kb mRNA was expressed, and it was more significant than the 2.1kb mRNA in heart and skeletal muscle. The TPA-induced monocytic differentiation of U937, which also resulted in growth arrest, abruptly downregulated the expression of 3-PGDH. Removal of TPA restored cell growth through the retrodifferentiation process and subsequent expression of 3-PGDH. The 3-PGDH mRNA was markedly expressed in human leukemias, lymphoma Sup-T1, colon adenocarcinoma COLO 320DM, epitheloid carcinoma HeLa S3, and murine lymphoma BW5147.G.1.4, but not in human leukemia K562. This report demonstrates that the human 3-PGDH gene is regulated at the transcriptional level depending on tissue specificity and cellular proliferative status, and its transcriptional regulation mechanism may be a useful target for diagnosis and therapy of cancer (10713460).
PMID 10713460

Tissue/Cells

| | | | |
|---|---|---|---|
| Brain | Cerebrospinal fluid | Colon | Endometrium |
| Fibroblasts | Kidney | Liver | Lymphoblasts |
| Lymphocytes | Ovary | Pancreas | Prostate |
| Testis | | | |

FIG. 22B

(Cytosol) 3-phospho-D-glycerate + NAD$^+$ = 3-phosphohydroxypyruvate + NADH

Location Cytosol
Catalyst 1.1.1.95
Cofs
Revers No

| Chem | StC | CoenzType |
|---|---|---|
| 3-phospho-D-glycerate | 1 | |
| NADH | -1 | donor |
| NAD('+) | 1 | acceptor |
| 3-phosphohydroxypyruvate | -1 | |

Annotations

EC 1.1.1.95 Phosphoglycerate dehydrogenase

Names

3-Phosphoglycerate dehydrogenase
3-Phosphoglycerate:NAD+ 2-oxidoreductase
3-Phosphoglyceric acid dehydrogenase
alpha-Phosphoglycerate dehydrogenase
D-3-Phosphoglycerate dehydrogenase
D-3-Phosphoglycerate:NAD oxidoreductase
Dehydrogenase, phosphoglycerate
Glycerate 3-phosphate dehydrogenase
Glycerate-1,3-phosphate dehydrogenase
Phosphoglycerate dehydrogenase
Phosphoglycerate oxidoreductase
Phosphoglyceric acid dehydrogenase

Human genes assigned:

| Symbol | Name | SwissProt | UniGene |
|--------|------|-----------|---------|
| PHGDH | 3-phosphoglycerate dehydrogenase | O43175 | Hs.3343 |

Pathways & Reactions

Reactions (Cytosol) 3-phospho-D-glycerate + $NAD^+$ = 3-phosphohydroxypyruvate + NADH

Pathways 3-phospho-D-glycerate/L-glutamate//2-oxoglutarate/L-serine//cyt

Annotations

1
Diseases    3-phosphoglycerate dehydrogenase deficiency, carcinoma
Note
PMID        3126791
Tissue/Cells Colon

FIG. 24A

EC 1.1.1.95 Phosphoglycerate dehydrogenase

Diseases 3-phosphoglycerate dehydrogenase deficiency
Note 3-Phosphoglycerate dehydrogenase (3-PGDH) deficiency is an inborn error of serine biosynthesis. Patients are affected with congenital microcephaly, psychomotor retardation, and intractable seizures. The effects of oral treatment with amino acids were investigated in 2 siblings. L-Serine up to 500 mg/kg/day was not sufficient for seizure control. Addition of glycine 200 mg/kg/day resulted in complete disappearance of seizures. Electroencephalographic abnormalities gradually resolved after 6 months. We conclude that 3-PGDH can be treated effectively by a combination of L-serine and glycine.
PMID 8758134, 9708551
Tissue/Cells N/A

3

Diseases cancer susceptibility, prostate and brain, carcinoma, leukemia, lymphoma
Note The nucleotide sequence of Hs 3-PGDH gene, encoding human 3-phosphoglycerate dehydrogenase that catalyzes the initiating step in the phosphorylated pathway of serine biosynthesis, has been determined. The 3-PGDH gene has a predicted 533 amino acid open reading frame, encoding a 56.8kDa protein that shares 94.0% similarity with rat-liver 3-PGDH. Two different transcripts corresponding to 3-PGDH mRNA were detected in human normal tissues. A dominant 2.1kb transcript was expressed at high levels in prostate, testis, ovary, brain, liver, kidney, and pancreas, and weakly expressed in thymus, colon, and heart. A 710bp transcript also appeared as a weaker band where the 2.1kb mRNA was expressed, and it was more significant than the 2.1kb mRNA in heart and skeletal muscle. The TPA-induced monocytic differentiation of U937, which also resulted in growth arrest, abruptly downregulated the expression of 3-PGDH. Removal of TPA restored cell growth through the retrodifferentiation process and subsequent expression of 3-PGDH. The 3-PGDH mRNA was markedly expressed in human leukemias, lymphoma Sup-T1, colon adenocarcinoma COLO 320DM, epitheloid carcinoma HeLa S3, and murine lymphoma BW5147.G.1.4, but not in human leukemia K562. This report demonstrates that the human 3-PGDH gene is regulated at the transcriptional level depending on tissue specificity and cellular proliferative status, and its transcriptional regulation mechanism may be a useful target for diagnosis and therapy of cancer (10713460).
PMID 10713460
Tissue/Cells Prostate, Testis, Liver, Ovary, Brain, Pancreas, Kidney

FIG. 24B

(Cytosol) 3-phosphohydroxypyruvate + L-glutamate = `O`-phospho-L-serine + 2-oxoglutarate Location Cytosol
Catalyst 2.6.1.52
Cofs
Revers No

| Chem | StC | CoenzType |
|---|---|---|
| `O`-phospho-L-serine | -1 | |
| 2-oxoglutarate | -1 | |
| L-glutamate | 1 | |
| 3-phosphohydroxypyruvate | 1 | |

Annotations

EC 2.6.1.52 Phosphoserine transaminase

Names

3-Phosphoserine aminotransferase
Aminotransferase, phosphoserine
Hydroxypyruvic phosphate-glutamic transaminase
L-Phosphoserine aminotransferase
O-Phospho-L-serine:2-oxoglutarate aminotransferase
Phosphohydroxypyruvate transaminase
Phosphohydroxypyruvic-glutamic transaminase
Phosphoserine aminotransferase
Phosphoserine transaminase
PSAT

Human genes assigned:

| Symbol | Name | SwissProt | UniGene |
|---|---|---|---|
| PSA | phosphoserine aminotransferase | Q9Y617 | Hs.286049 |

Pathways & Reactions

Reactions

(Cytosol) 3-phosphohydroxypyruvate + L-glutamate = O-phospho-L-serine + 2-oxoglutarate

Pathways

3-phospho-D-glycerate/L-glutamate//2-oxoglutarate/L-serine//cyt

Annotations

1
Diseases
Note
PMID 6089514,2682527
Tissue/Cells Lymphocytes, Endometrium 2
Diseases
Note In particular in tissues with a high rate of cell turnover, phosphoserine aminotransferase and serine hydroxymethyltransferase activities were coordinately increased (6089514).
PMID 6089514
Tissue/Cells N/A

FIG. 26

(Cytosol) `O`-phospho-L-serine + $H_2O$ = L-serine + phosphate

Location  Cytosol
Catalyst  3.1.3.3
Cofs
Revers    No

| Chem | StC | CoenzType |
|---|---|---|
| H(,2)O | 1 | |
| `O`-phospho-L-serine | 1 | |
| L-serine | -1 | |
| phosphate | -1 | |

Annotations

EC 3.1.3.3 phosphoserine phosphatase

Names

3-phosphoserine phosphatase
O-phosphoserine phosphohydrolase
phosphatase, phosphoserine
phosphoserine phosphatase
PSP
PSPase

Human genes assigned:

| Symbol | Name | SwissProt | UniGene |
|--------|------|-----------|---------|
| PSPH | phosphoserine phosphatase | P78330 | Hs.56407 |

Pathways & Reactions

Reactions

(Cytosol) 'O'-phospho-L-serine + $H_2O$ = L-serine + phosphate

Pathways

3-phospho-D-glycerate/L-glutamate//2-oxoglutarate/L-serine//cyt

FIG. 28

Gene PSPH

Symbols PSPH PSP
Location 07 p21-15
Names phosphoserine phosphatase
OMIM 172480
Enzyme 3.1.3.3
GDB 120322
SwissProt P78330
UniGene Hs.56407
Sequences Y10275

Expressed in adrenal gland; aorta; bone; bone marrow; brain; cervix; colon; colon_est; eye; kidney; liver; lung; muscle (skeletal); nervous_tumor; pancreas; placenta; pool; pooled lung and spleen; prostate; stomach; thyroid; whole embryo

Amino Acid Sequence

MISHSELRKLFYSADAVCFDVDSTVIREEGIDELAKICGVEDAVSEMTRRAMGGAVPFKAALTERLALIQPSREQVQRLIAEQP

Number of ESTs from different organs/tissues (fetal ESTs and those without explicit organ/tissue data are exclude

| Liver | Brain | Kidney | Heart | Lung | Total |
|---|---|---|---|---|---|
| 2 | 24 | 2 | 0 | 4 | 61 |
| 3% | 39% | 3% | 0% | 6% | 100% |

Expressed sequence tags (ESTs)

(20 out of 90) ... view full list
AA488432  AA488571  AA621925  AI370893  AI479788  AL525152  AL526979  AL527020  AL528007  AL52917
AL562450  AL563029  AL563371  AU118817  AU124836  AU143638  AU148622  AU160327  AU160699  AW0295:

FIG. 29

SWISS-PROT: P78330

| ExPASy Home page | Site Map | Search ExPASy | Contact us | SWISS-PRC |

Hosted by NCSC US | Mirror sites: | Australia | Canada | China | Korea | Switzerland | Taiwan

SWISS-PROT: P78330

*NiceProt* - *a user-friendly view of this SWISS-PROT entry*

```
ID   SERB_HUMAN      STANDARD;      PRT;    225 AA.
AC   P78330;
DT   30-MAY-2000 (Rel. 39, Created)
DT   30-MAY-2000 (Rel. 39, Last sequence update)
DT   16-OCT-2001 (Rel. 40, Last annotation update)
DE   L-3-phosphoserine phosphatase (EC 3.1.3.3) (PSP) (O-phosphoserine
DE   phosphohydrolase) (PSPase).
GN   PSPH.
OS   Homo sapiens (Human).
OC   Eukaryota; Metazoa; Chordata; Craniata; Vertebrata; Euteleostomi;
OC   Mammalia; Eutheria; Primates; Catarrhini; Hominidae; Homo.
OX   NCBI_TaxID=9606;
RN   [1]
RP   SEQUENCE FROM N.A.
RX   MEDLINE=97332542; PubMed=9188776; [NCBI, ExPASy, EBI, Israel, Japan]
RA   Collet J.-F., Gerin I., Rider M.H., Veiga-Da-Cunha M.,
RA   Van Schaftingen E.;
RT   "Human L-3-phosphoserine phosphatase: sequence, expression and
RT   evidence for a phosphoenzyme intermediate.";
RL   FEBS Lett. 408:281-284(1997).
CC   -!- FUNCTION: CATALYZES THE LAST STEP IN THE BIOSYNTHESIS OF SERINE
CC       FROM CARBOHYDRATES. THE REACTION MECHANISM PROCEEDS VIA THE
CC       FORMATION OF A PHOSPHORYL-ENZYME INTERMEDIATES.
CC   -!- CATALYTIC ACTIVITY: Phosphoserine + H(2)O = serine + phosphate.
CC   -!- COFACTOR: MAGNESIUM.
CC   -!- SUBUNIT: HOMODIMER.
CC   -!- SIMILARITY: BELONGS TO THE SERB FAMILY.
CC   -------------------------------------------------------------------
CC   This SWISS-PROT entry is copyright. It is produced through a collaboration
CC   between the Swiss Institute of Bioinformatics and the EMBL outstation -
CC   the European Bioinformatics Institute. There are no restrictions on its
CC   use by non-profit institutions as long as its content is in no way
CC   modified and this statement is not removed. Usage by and for commercial
CC   entities requires a license agreement (See http://www.isb-sib.ch/announce/
CC   or send an email to license@isb-sib.ch).
CC   -------------------------------------------------------------------
DR   EMBL; Y10275; CAA71318.1; -.  [EMBL / GenBank / DDBJ] [CoDingSequence]
DR   MIM; 172480; -.  [NCBI / EBI]
DR   GeneCards; PSPH.
DR   GeneLynx; PSPH.
DR   Ensembl; P78330.
DR   SOURCE; PSPH.
DR   InterPro; IPR001454; Hignase/hydrlase.
DR   InterPro; IPR004469; SerB.
DR   InterPro; Graphical view of domain structure.
DR   Pfam; PF00702; Hydrolase; 1.
DR   TIGRFAMs; TIGR00338; serB; 1.
DR   ProDom [Domain structure / List of seq. sharing at least 1 domain]
DR   BLOCKS; P78330.
DR   ProtoMap; P78330.
DR   PRESAGE; P78330.
```

FIG. 30A

SWISS-PROT: P78330

```
DR    DIP; P78330.
DR    ModBase; P78330.
DR    SWISS-2DPAGE; GET REGION ON 2D PAGE.
KW    Hydrolase; Serine biosynthesis; Magnesium; Phosphorylation.
SQ    SEQUENCE    225 AA;   25022 MW;   ECE5C34255F5D115 CRC64;
      MISHSELRKL FYSADAVCFD VDSTVIREEG IDELAKICGV EDAVSEMTRR AMGGAVPFKA
      ALTERLALIQ PSREQVQRLI AEQPPHLTPG IRELVSRLQE RNVQVFLISG GFRSIVEHVA
      SKLNIPATNV FANRLKFYFN GEYAGFDETQ PTAESGGKGK VIKLLKEKFH FKKIIMIGDG
      ATDMEACPPA DAFIGFGGNV IRQQVKDNAK WYITDFVELL GELEE
//
```

*P78330 in FASTA format*
*NiceProt - a user-friendly view of this SWISS-PROT entry*
*View entry in raw text format (no links)*
*Report form for errors/updates in this SWISS-PROT entry*

---

 Direct BLAST submission at EMBnet-CH/SIB (Switzerland)    Direct BLAST submission at NCBI (Bethesda, USA)

 ScanProsite, MotifScan     Tools  Sequence analysis tools: ProtParam, ProtScale, Compute pI/Mw, PeptideMass, PeptideCutter, Dotlet (Java)

 Feature table viewer (Java)     Search the SWISS-MODEL Repository

| ExPASy Home page | Site Map | Search ExPASy | Contact us | SWISS-PRO]|
| --- | --- | --- | --- | --- |
| Hosted by NCSC US | Mirror sites: | Australia Canada China | Korea Switzerland | Taiwan |

FIG. 30B

NCBI-UniGene

UniGene

PubMed  Entrez  BLAST  OMIM  Taxonomy  Structure
Search Human [Go]

NCBI  UniGene Cluster Hs.56407 *Homo sapiens*

UniGene         PSPH Phosphoserine phosphatase

Home Page       SEE ALSO
                LocusLink:  5723
Frequently Asked  OMIM:      172480
Questions       HomoloGene: Hs.56407

Query Tips      SELECTED MODEL ORGANISM PROTEIN SIMILARITIES
DDD-Library     organism, protein and percent identity and length of aligned
Digital Differential  region
Display         H.sapiens:    ref:NP_004568.1 - L-3-              99 % / 224 aa
                              phosphoserine phosphatase          (see ProtEST)
Download        A.thaliana:   pir:T51362 - T51362 phosphoserine  50 % / 223 aa
UniGene                       phosphatase (EC 3.1.3.3) precursor, (see ProtEST)
                              chloroplast [validated] - Arabidopsis
                              thali
UniGene         C.elegans:    ref:NP_502581.1 - Y62E10A.13b.p    47 % / 234 aa
Homo sapiens                  [Caenorhabditis elegans]           (see ProtEST)
Home Page       D.melanogaster: ref:NP_524001.1 - astray         50 % / 213 aa
                              [Drosophila melanogaster]          (see ProtEST)
Release Statistics  E.coli:   sp:P06862 - SERB_ECOLI             32 % / 176 aa
                              Phosphoserine phosphatase (PSP)    (see ProtEST)
Library Report                (O-phosphoserine
                              phosphohydrolase) (PSPase)
Library Browser S.cerevisiae: pir:S53931 - S53931 phosphoserine  30 % / 193 aa
DDD-Library                   phosphatase (EC 3.1.3.3) - yeast   (see ProtEST)
Digitial Differential         (Saccharomyces cerevisiae)
Display
                MAPPING INFORMATION
                Chromosome:   7
                OMIM Gene Map: 7p21-p15
UniGene Animals UniSTS entries: A002S16  Genomic Context: Map View
Anopheles       UniSTS entries: D11938   Genomic Context: Map View
gambiae
                EXPRESSION INFORMATION
Bos taurus      cDNA sources: adenocarcinoma;adenocarcinoma, cell line;adrenal
                              cortex carcinoma, cell line;anaplastic
Danio rerio                   oligodendroglioma with 1p/19q
                              loss;aorta;ascites;astrocytoma grade iv, cell
Drosophila                    line;brain;cervical carcinoma cell
melanogaster                  line ;colon;colon_est;embryonal carcinoma, cell
                              line;epithelioid carcinoma;from chronic myelogenous
Homo sapiens                  leukemia;glioblastoma;hypernephroma;hypothalamus,
                              cell line;insulinoma;kidney;large cell carcinoma;large
Mus musculus

FIG. 31A

NCBI-UniGene

Rattus norvegicus

Xenopus laevis

UniGene Plants

Arabidopsis thaliana

Hordeum vulgare

Oryza sativa

Triticum aestivum

Zea mays

Related Resources

Human Genome Guide

LocusLink

HomoloGene dbEST-Database of Expressed Sequence Tags

Cancer Genome Anatomy Project

I.M.A.G.E. Quality Control cell carcinoma, undifferentiated;lung;lung focal fibrosis;lymph;lymphoma, cell line;melanotic melanoma;mucoepidermoid carcinoma;muscle (skeletal);nervous_tumor;neuroblastoma cells;osteosarcoma, cell line;placenta;pool;pooled colon, kidney, stomach;pooled lung and spleen;primitive neuroectoderm;retinoblastoma;stomach;thyroid;whole embryo;whole embryo, mainly head SAGE : Gene to Tag mapping mRNA SEQUENCES (2)

| NM_004577 | Homo sapiens phosphoserine phosphatase (PSPH), mRNA | P A |
| Y10275 | H.sapiens mRNA for L-3-phosphoserine phosphatase | P A |

EST SEQUENCES (10 of 101)[Show all ESTs]

| BF696598 | cDNA clone IMAGE:4282223 | primitive neuroectoderm | 5' read | P M |
| BF699126 | cDNA clone IMAGE:4283629 | primitive neuroectoderm | 5' read | P M |
| BF669381 | cDNA clone IMAGE:4277659 | primitive neuroectoderm | 5' read | P M |
| BF700423 | cDNA clone IMAGE:4287566 | primitive neuroectoderm | 5' read | P M |
| BF669233 | cDNA clone IMAGE:4277012 | primitive neuroectoderm | 5' read | P M |
| BE543892 | cDNA clone IMAGE:3457797 | cervical carcinoma cell line | 5' read | P M |
| BF699165 | cDNA clone IMAGE:4283568 | primitive neuroectoderm | 5' read | P M |
| BE257645 | cDNA clone IMAGE:3353678 | retinoblastoma | 5' read | P M |
| BI223114 | cDNA clone IMAGE:5104424 | cervical carcinoma cell line | 5' read | P M |
| BE251421 | cDNA clone IMAGE:3356614 | retinoblastoma | 5' read | P M |

Key to Symbols

P Has similarity to known Proteins (after translation)
A Contains a poly-Adenylation signal
M Clone is putatively CDS-complete by MGC criteria

DOWNLOAD SEQUENCES

There will be a pause of up to one minute before your computer receives any data. The default filename will be "download" If your operating system responds to filename suffixes, remember to choose a

FIG. 31B

NCBI-UniGene suffix compatible with plain text or fasta formats.

Unix [ Download sequences ]

switch to text mode

NLM|NIH|UniGene| Privacy Statement |Disclaimer| NCBI Help

FIG. 31C

SYSTEM RECONSTRUCTION: INTEGRATIVE ANALYSIS OF BIOLOGICAL DATA

This application claims the benefit under 35 U.S.C. §119(e) of U.S. Provisional Patent Application No. 60/299,040 filed on Jun. 18, 2001, by Nikolskaya et al., entitled "Competitive Analysis of EST Data and Functional Reconstruction Technology," which is incorporated herein by reference.

FIELD OF THE INVENTION

The present invention relates to bioinformatics technologies. More specifically, the present invention relates to the technology of System Reconstruction.

BACKGROUND

The past few years have seen dramatic advances in genomics and other areas of "high-throughput" biology. The fruits of these accelerated technologies culminated in last-year's publication of the human genome. (Venter et al., (2001) The sequence of the human genome, Science. 291: 1304-1351.) The availability of the DNA sequence of the human genome promises to alleviate much of human suffering from life-threatening diseases. Knowledge of an entire genome may lead to the discovery of new drug targets. Access to the DNA sequence of an individual promises to reduce drug side effects and to allow tailoring medicine to the individual's genetic makeup. Both government agencies and drug companies have invested heavily in these technologies. In return, they expected to vastly reduce the cost and time of drug development, a process costing on average over $500 million in the 1990s and usually spanning over a decade from the initial discovery of drug targets and leads, through validation, optimization, and finally clinical trials.

Currently, these expectations are far from reality because human biology is complex, and there has been no systematic approach to capture this biological complexity. A new field of computational biology has been forged to make sense out of the inordinate amount of genomics data—including DNA sequence data, gene expression data, proteomics, metabolomics, and cellomic data. It is believed by many in the industry that the integration of these data alone would quickly lead to the correlation of phenotype (clinical manifestations) with genotype (variations in gene sequence). That goal is still far off, however, as the majority of these data are examined out of context. The basis of a disease cannot be understood without understanding, for example, the alternative splicing forms of the related genes, the proteins for which they code, the complex networks of protein interactions involved, the multiple levels of gene regulation and expression, the correlations between healthy and diseased tissue, the significance of clinical data, and the like. The complexity of human biology requires a systemic understanding of genomic data rather than a shotgun understanding. As a result, the field of systems biology arose and is rapidly becoming a leading approach to understanding human biology.

There are a number of public and commercial efforts that have focused on characterizing various aspects of general biochemistry and metabolism. Some of these databases include KEGG (Kanehisa et al., (2002) The KEGG databases at GenomeNet, Nucleic Acids Res., 30: 42-46); BRENDA (Schomburg et al., (2002) BRENDA, Enzyme data and metabolic information, Nucleic Acids Res., 30: 47-49); SWISS-PROT (Bairoch and Apweiler, (2000) The SWISS-PROT protein sequence database and its supplement TrEMBL in 2000, Nucleic Acids Res. 28: 45-48); EcoCyc (Karp et al., (2002) The EcoCyc Database, Nucleic Acids Res. 30: 56-8); and EMP/MPW (Selkov et al., (1998) MPW: the Metabolic Pathways Database, Nucleic Acids Res., 26: 43-45). None of these databases, however, focus specifically on human, or on a single species.

The technology known as Metabolic Reconstruction was developed by Dr. Evgeni Selkov and co-workers at the Argonne National Laboratory. Metabolic Reconstruction was developed to study an organism's metabolism by using its genome sequence. (Selkov, et al., (1997) A reconstruction of the metabolism of Methanococcus jannaschii from sequence data, Gene, 197, GC11-26).

Traditionally, it has not been considered feasible to study metabolism based on EST data. Such an approach, however, would be very useful for comparative analyses of complex eukaryotic genomes. First, generation of a complete set of ESTs is at least an order of magnitude less expensive than whole genome sequencing. Second, there is a great deal of processed EST data freely available to the scientific community. Currently, there are only a few complete eukaryotic genomes available to the public, but there are sufficient EST data for several dozens of species. Third, and most important, ESTs represent genes that are expressed at specific times in specific tissues. In the present invention, expressed sequence tag data, rather than genomic sequences, were used to reconstruct various aspects of human metabolism.

SUMMARY OF THE INVENTION

The process of the present invention, referred to as System Reconstruction, integrates data on organism- and tissue-specific biochemical pathways, genome sequences, conditional gene expression, and genetic polymorphisms with clinical manifestations of diseases and other clinical traits. As a result, a network of interconnected functional pathways (a Functional or System Model) is constructed in which elements are linked to appropriate molecular data (ORFs, ESTs, SNPs, etc.) and annotated with relevant clinical information.

Generally, the first step in creating a System Reconstruction model is the determination of a network of relevant biochemical pathways, specific for certain human tissues at certain developmental stages (Metabolic Reconstruction). Next, the collection of pathways is extended by computational reconstruction of relevant metabolic networks. Third, the expression data is integrated into the resulting metabolic map to generate a "snap shot" for any specific cell, organ, or tissue. Comparison of such "snap shots" constructed for the same tissue in normal and disease states (or in different developmental stages), provides valuable information about regulatory mechanisms of the disease or of development. Finally, the System Reconstruction model is completed by integrating the developmental pathways and mapping them onto the metabolic network. This step verifies the regulatory pathways and completes the functional overview of the network.

The present invention relates to a method for determining necessary functions involved in a particular metabolic pathway. In one aspect, the present invention provides a visual overview of expressed genes associated with a particular pathway specific for normal and abnormal human tissues. The present invention can also provide a method for determining and identifying the ORFs involved in those pathways. The present invention further provides a method for comparing System Reconstructions made for normal and diseased organs or tissues, thus providing important information about possible regulatory mechanisms and potential drug targets.

In another aspect, the present invention provides a method for comparing the reconstructions made for the same tissues at different developmental stages, thus providing information about the developmental timing of gene expression and revealing possible targets for gene therapy.

In another aspect, the present invention provides a method for mapping single nucleotide polymorphism (SNP) sites to corresponding metabolic genes and/or predicted ORFs, thus providing physiological insights into associations of SNPs with unknown phenotypes.

The present invention also relates to the determination of complicated cellular networks using abundant gene expression data (such as EST and micro-array data) as well as genomic sequence data; the identification of relationships between different human genes, pathways and parts of metabolism the identification and grouping according to function of over- and under-expressed genes specific for given tissue or condition; the generation of interactive, integrated functional outlines for all parts of human metabolism.

BRIEF DESCRIPTION OF THE DRAWINGS

FIG. 9A is an example of an enzyme page for methionine adenosyltransferase.

FIG. 9B is an example of an enzyme page for methionine adenosyltransferase (continued from FIG. 9A).

FIG. 10 is an example of a reaction page.

FIG. 11 is an example of a gene page.

FIG. 12 is an example of a compound page.

FIG. 17 shows a Parkinson disease page.

FIG. 22A shows notes associated with the serine biosynthesis scheme (3-phospho-D-glycerate/L-glutamate//2-oxoglutarate/L-serine//cyt).

FIG. 22B shows notes associated with the serine biosynthesis scheme (3-phospho-D-glycerate/L-glutamate//2-oxoglutarate/L-serine//cyt) continued from FIG. 22A.

FIG. 23 illustrates reaction 1 from the serine biosynthesis scheme [(Cytosol) 3-phospho-D-glycerate+NAD+=3-phosphohydroxypyruvate+NADH].

FIG. 24A is an enzyme page for EC 1.1.1.95, phosphoglycerate dehydrogenase.

FIG. 24B is an enzyme page for EC 1.1.1.95, phosphoglycerate dehydrogenase continued from FIG. 24A.

FIG. 25 illustrates reaction 2 from the serine biosynthesis scheme [(Cytosol) 3-phosphohydroxypyruvate+L-glutamate='O'-phospho-L-serine+2-oxoglutarate].

FIG. 26 is an enzyme page for EC 2.6.1.52, phosphoserine transaminase.

FIG. 27 illustrates reaction 3 from the serine biosynthesis scheme [(Cytosol) 'O'-phospho-L-serine+H2O=L-serine+phosphate].

FIG. 28 is an enzyme page for EC 3.1.3.3, phosphoserine phosphatase.

FIG. 29 is the Gene PSPH page for EC 3.1.3.3, phosphoserine phosphatase.

FIG. 30A is the SWISS-PROT: P78330 page for EC 3.1.3.3, phosphoserine phosphatase.

FIG. 30B is the SWISS-PROT: P78330 page for EC 3.1.3.3, phosphoserine phosphatase continued from FIG. 30A.

FIG. 31A is the UniGene Cluster Hs.56407 page for EC 3.1.3.3, phosphoserine phosphatase.

FIG. 31B is the UniGene Cluster Hs.56407 page for EC 3.1.3.3, phosphoserine phosphatase continued from FIG. 31A.

FIG. 31C is the UniGene Cluster Hs.56407 page for EC 3.1.3.3, phosphoserine phosphatase continued from FIGS. 31A and 31B.

DESCRIPTION OF THE PREFERRED EMBODIMENTS

A bioinformatics approach called System Reconstruction (described in co-pending U.S. Provisional Patent Application Ser. No. 60/299,040, which is incorporated herein by reference) is used to integrate clinical information with high-throughput molecular data. In the core of this approach, a collection of human tissue-specific and condition-specific biochemical pathways are linked by common intermediates into maps or models. These models serve as a framework to integrate complementary types of high-throughput data and to establish mechanisms underlying clinical manifestations of diseases.

Figure 1:
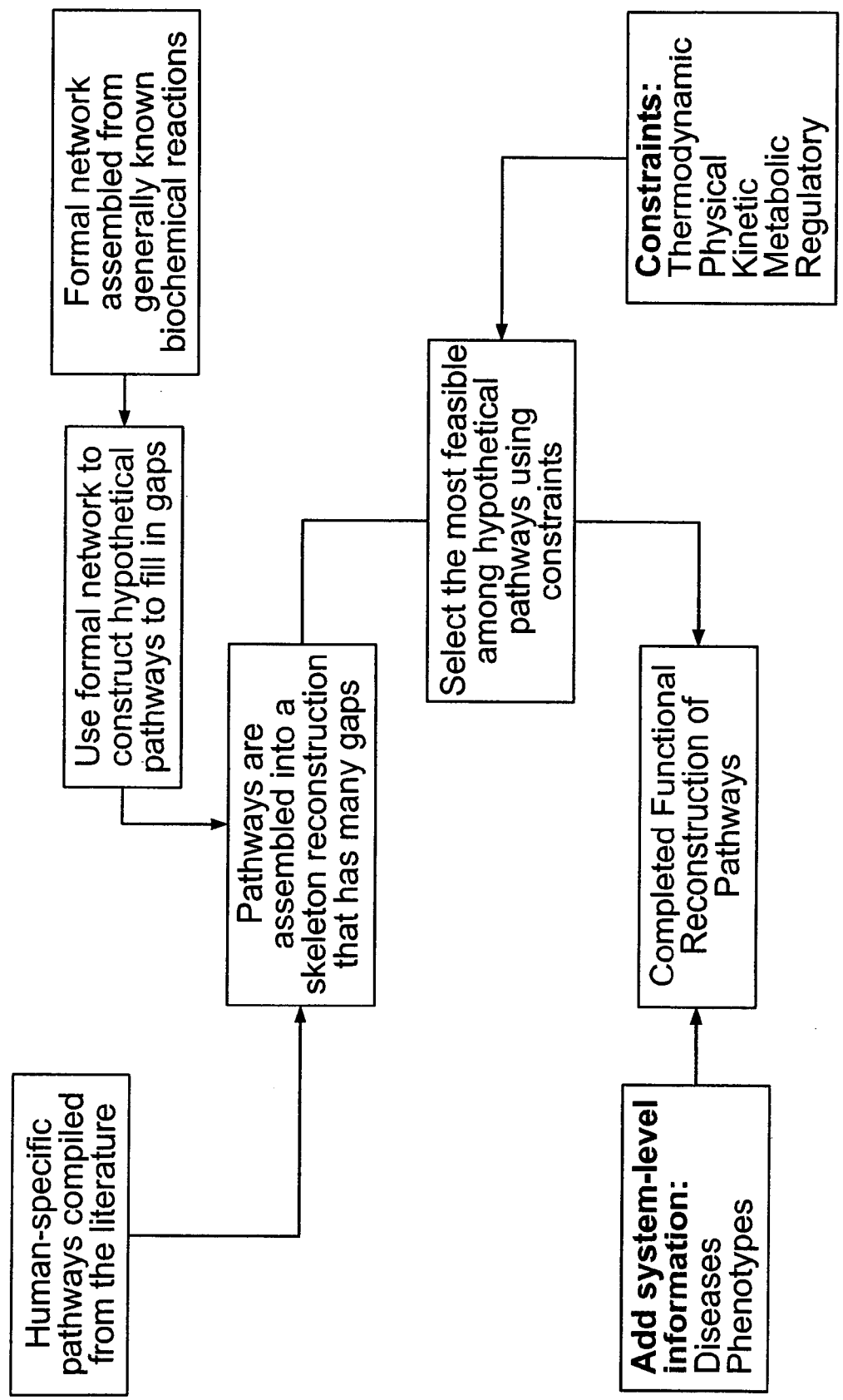
FIG. 1 is a schematic overview of the process of System Reconstruction.

The present invention creates a system that allows building human-specific system-level models of biochemistry. In summary, information regarding human-specific pathways is collected. The pathways are linked to functional information, disease manifestations, and high-throughput data. Finally, pathways are connected to each other and linked to relevant information to form a functional model. These models can be used, for example, as skeletons for further integration of high-throughput data, for deciphering mechanisms of diseases, for predicting drug metabolism and toxicity, and the like. System Reconstruction is a complex multi-step process that involves assembling a collection of human-specific pathways and results in fully annotated interactive maps of specific metabolic systems. See FIG. 1.

The process of System Reconstruction generally starts with the creation of a collection of metabolic pathways. Pathways that are human-specific and in the form in which they occur in humans are included. Building such a collection is achieved through a multi-level annotation process. Starting with a collection of identified metabolic pathways from mammals and non-mammals, the pathways are divided into categories based on relevance.

Currently, the database contains about 3300 pathways described in various species of mammals and about 2060 non-mammalian pathways. Of the mammalian pathways about 920 are multi-step pathways and the rest are single-step pathways. The pathways are divided into several categories according to the probability of their relevance to human metabolism. The most relevant category includes multi-step mammalian pathways for which all reactions are catalyzed by either identified human enzymes or enzymes that have ORF candidates in the human genome (about 710 pathways). The next category includes multi-step mammalian pathways that have human enzymes at the beginning and at the end of the pathway (about 40 pathways). In the next category, there are mammalian and non-mammalian multi-step pathways that contain human enzymes in the middle of the pathway (about 800 pathways). Finally, there are pathways with no identified human enzymes (about 1500 pathways).

In addition to these categories, there is a collection of single step reactions that can be catalyzed by human enzymes (about 2300 pathways) or by mammalian enzymes (over 5000 pathways). It should be noted, however, that not every such reaction which can be catalyzed by a human enzyme is in fact a functional human pathway. Many enzymes possess a broad spectrum of specificity in vitro, while in vivo there are many additional constraints that limit their functionality such as, for example, compartmentalization, absence of precursors, and kinetic competition.

The process of ranking, as described above, creates a working collection of pathways that are then annotated. The initial collection of pathways may contain many pathways that are similar to human pathways but still have essential differences. Some of the differences may be in cofactors or sub-cellular localization of enzymes and metabolites. Also, human versions of pathways may be truncated or contain additional steps when compared to pathways from other species. Since many enzymes show a range of specificity, they may substitute for each other in similar pathways from different species. Therefore, during the annotation process, the available literature for every pathway is reviewed to determine the human-specific form of the pathway. Pathways from the two most relevant categories are usually easy to verify through biomedical literature and generally require few, if any, modifications. The third category of pathways, as well as single step reactions with human enzymes, generally require a thorough literature search to be confirmed or rejected as human-specific pathways and usually undergo substantial changes. Finally, pathways with no human enzymes are left until the later stages when metabolic maps are built. At that point, some of those pathways are selected as candidate human pathways if they fit well into gaps in the map that can not be easily filled by pathways from higher ranking categories.

In addition to creating a collection of human specific pathways, the process of annotation yields important functional data about each pathway and its elements. In order to structure this information, a pathway is described as a hierarchy of "biochemical units." These units comprise the pathway itself, individual steps that make up the pathway, chemical compounds, reactions, and "enzymatic functions" that are involved in each step. "Enzymatic functions" are related, in turn, to molecular species-specific proteins and genes. In a process called structured annotation, links are established between particular "biochemical units" and specific categories and instances in other data fields, discussed in greater detail below. Practically, this is achieved by filling in annotation tables associated with each biochemical unit. Some examples of fields in these tables include: organ and tissue localization of the unit; intracellular localization and/or compartmentalization; existence and subcellular localization of the unit in other organisms; connection of the unit with inherited and common diseases and other functional disorders; type of relationship between the unit and a disease (e.g., cause, manifestation, and the like); and references on the information source.

Structured annotation allows the organization of heterogeneous data and the development of queries and computer algorithms that can track explicit and implicit links among these data. Some examples include finding compounds, enzymes, reactions, and pathways that are directly linked in a particular unit; automatically interconnecting pathways and reactions into networks based on shared intermediates or other links; establishing constraints on pathway interactions based on sub-cellular localization of their components; finding pathways, reactions compounds, and enzymes related to a disease, its causes or manifestations, and interconnecting such elements into a "disease network"; finding diseases related by common pathways, reactions, or compounds; finding alternative pathways for degradation or biosynthesis of specific compounds, to circumvent certain enzymes, and the like.

In order to organize the information collected in the process of reconstruction, a relational database has been developed using Oracle RDBMS. Unlike many biomedical databases which are centered around a certain theme (e.g., sequences, proteins, biochemical reactions, and the like), the database developed according to the present invention is a polythematic database that is built around several central data entities and relations among them. These central entities include, for example, enzymes, compounds, reactions, pathways, genes, and diseases. By focusing on the relationships among entities, a functional database is developed.

Thus, in the architecture of the database, functions can have a role as space-holders (FIG. 3) to which additional molecular data are linked as they are discovered. Functions therefore are "linking portals" for heterogeneous data, such as gene expression, protein interactions, metabolite profiles, and the like. Once linked, these data become a part of a large system-level picture in which functional relations among the data can be elucidated.

Figure 3:
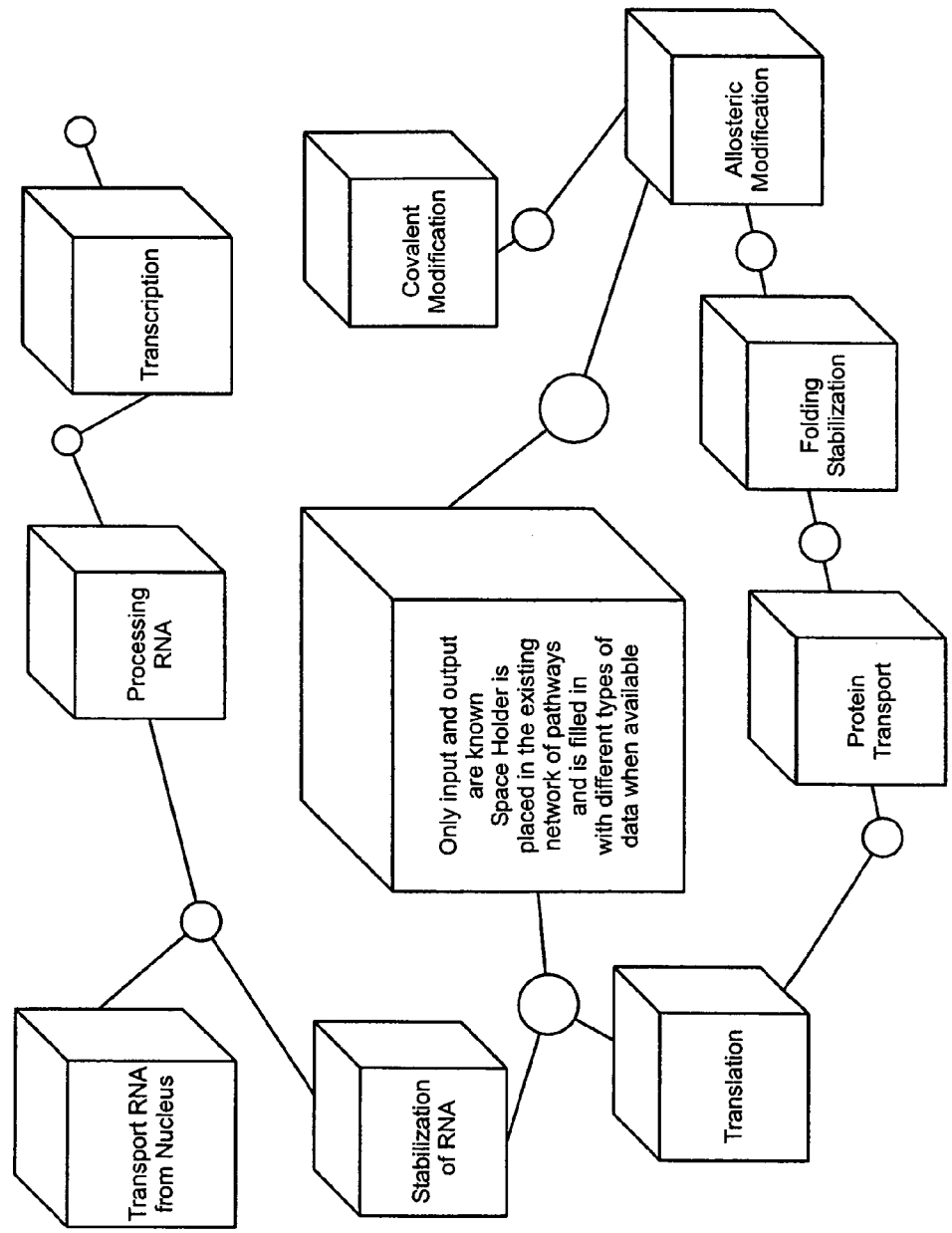
FIG. 3 is a chart illustrating the function of space holders in a System Reconstruction database.

As illustrated in FIG. 3, processes or functions act as space-holders for any molecular, mechanistic, dynamic, or other type of data that may be discovered later. Often, biological phenomena are initially described as set of inputs and outputs, or actions and responses, with little or no knowledge of the underlying mechanism or the molecular entities involved. In a database according to the present invention, it is possible to place such phenomena into the context of other processes by matching inputs and outputs. The resulting network links processes together based on these inputs and outputs, even when little detailed knowledge is available. As additional data become available, they are linked to the corresponding processes. Thus, the use of such space-holders allows heterogeneous data that have little overlap to be integrated into the self-consistent system-level picture.

Preferably, the database architecture accounts for various complexities of metabolism. For example, most enzymes can catalyze a range of reactions, and many reactions can be catalyzed by more than one enzyme. This multiplicity is preferably represented in a System Reconstruction database. As another example, there is usually more than one gene that corresponds to an enzyme or enzymatic function. There are currently about 2000 human genes assigned to enzymes corresponding to about 800 EC numbers. This type of multiplicity can also be represented in a database according to the present invention.

The next step is the building of functional models of specific categories of human metabolism, diseases, and other system-level reconstructions. Two important steps are (1) selecting a subset of the relevant pathways, and (2) linking them into metabolic networks. The selection of pathways is done by a set of "SELECT . . . FROM . . . WHERE . . . " type queries, relying on the information collected in the structured annotation tables discussed above. The information on links among pathways is implicitly contained in the database. For example, whenever two pathway records share a common intermediate, or when an intermediate in one pathway occurs as a regulatory factor in a record for an enzyme from another pathway, a link is generated between the two pathways. Further computations are facilitated when such links are translated into explicit relations among pathways. To this end, stoichiometric matrices that represent the participation of compounds in the reactions are assembled. Using these matrices, it is possible to find links among reactions and, since reactions are already related to pathways in the database, a network of interconnected pathways can be generated.

At this stage, such networks are considered crude skeletons and are likely to contain substantial gaps as well as many nonfunctional links among pathways. A careful review and modification is undertaken to develop approved functional models. To fill in gaps, a set of candidate pathways is chosen from pathways of closely related organisms as well as from hypothetical pathways, and constructed by formally linking reactions. Then genomic DNA and ESTs are used as additional evidence to validate the proposed pathways.

It should be noted that the quality of stand-alone eukaryotic ESTs is often not sufficient for unambiguous functional assignments. However, if functional assignments are done with additional constraints imposed by a skeletal functional model, the ambiguity generally can be eliminated. In other words, an initial functional model provides insight into the "work-plan" of a specific biochemical system, thereby allowing other data to be analyzed within the context of this work-plan.

At this stage, sets of enzymatic functions that participate in the hypothesized pathways are identified and a determination is made as to which ones can be verified by sequence and expression data. Those that are supported by this evidence are added to the model as proposed pathways. It is also possible to consider other types of high-throughput data including metabolic profiles, two-hybrid assays, and other types of data to further validate these pathways. The proposed pathways can become primary targets for further experimental research. For the resulting network, the information on diseases associated with pathways, enzymes, and compounds is extracted from structured annotations and explicitly related to corresponding elements. The reconstruction is represented as an interactive map from which other information can be accessed, as described below.

The database developed according to the present invention can address various problems that often result from the traditional view of metabolism. The database can provide a representation of a wide spectrum of enzyme activity. Current enzyme nomenclature is built on the assumption that there is a single enzyme for each enzymatic reaction. This assumption is not always true in practice. Many enzymes can catalyze a range of reactions, and many reactions can be catalyzed by more than one enzyme. The database developed according to the present invention can represent this multiplicity by introducing "many-to-many" relations between enzymes and reactions.

The database can reflect the relationships between "enzymatic function" and molecular species. The term "enzyme" is somewhat ambiguous. While some biologists apply it to a particular protein—a molecule of certain chemical composition (or a complex of a few proteins), others refer to the function itself—an ability to catalyze a certain type of reaction. In the data model according to the present invention, this ambiguity is avoided by establishing several entities that are related to the term "enzyme". One such is "enzymatic function" which is an ability to catalyze a certain reaction or class of reactions. Enzyme nomenclature and EC numbers are used to classify functions. Relating to any given function, there are specific molecular entries, such as proteins and genes. This system avoids the ambiguity that can occur when a single protein may possess a spectrum of catalytic activities, or when there may be more than one protein capable of catalyzing a certain reaction. In addition to avoiding ambiguity, such a data model is extremely useful in the process of functional annotation. For example, a disease that is linked to an enzymatic deficiency could have many potential causes, such as a mutation in the gene coding for the enzyme, problems at the gene expression level, or protein misfolding, to name a few. This expanded data model allows the association of a clinical trait with the appropriate specific data entity.

The database also addresses the compartmentalization and localization of enzymes and metabolites. In living cells, reactions take place in certain compartments and intracellular localizations. This is one of the major mechanisms that cells use to regulate intracellular processes. Many enzymes have a fairly broad spectrum of substrates. Specificity is often determined by co-localization of an enzyme and one of its substrates. In some cases, incorrect protein localization is implicated in a disease. This type of information is included in the database by developing a representation of cellular anatomy. Preferably, compartments and organelles found in different cell types and their mutual arrangement are reflected in the database. Spatial organization of metabolic processes is represented by establishing relationships between anatomical data and data on pathways, reactions, enzymes, and compounds.

Figure 4:
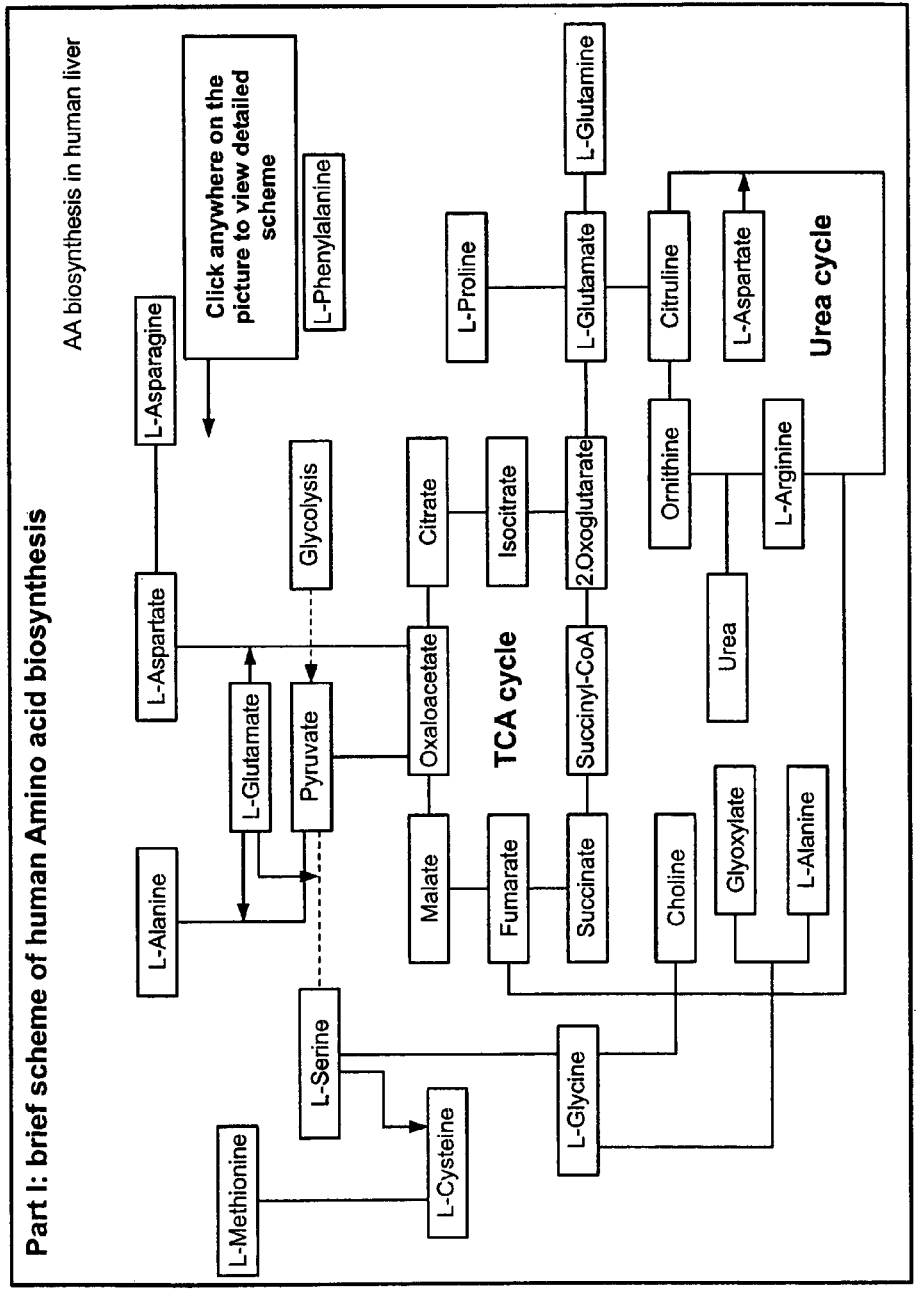
FIG. 4 illustrates a brief scheme of human amino acid biosynthesis.
Figure 5:
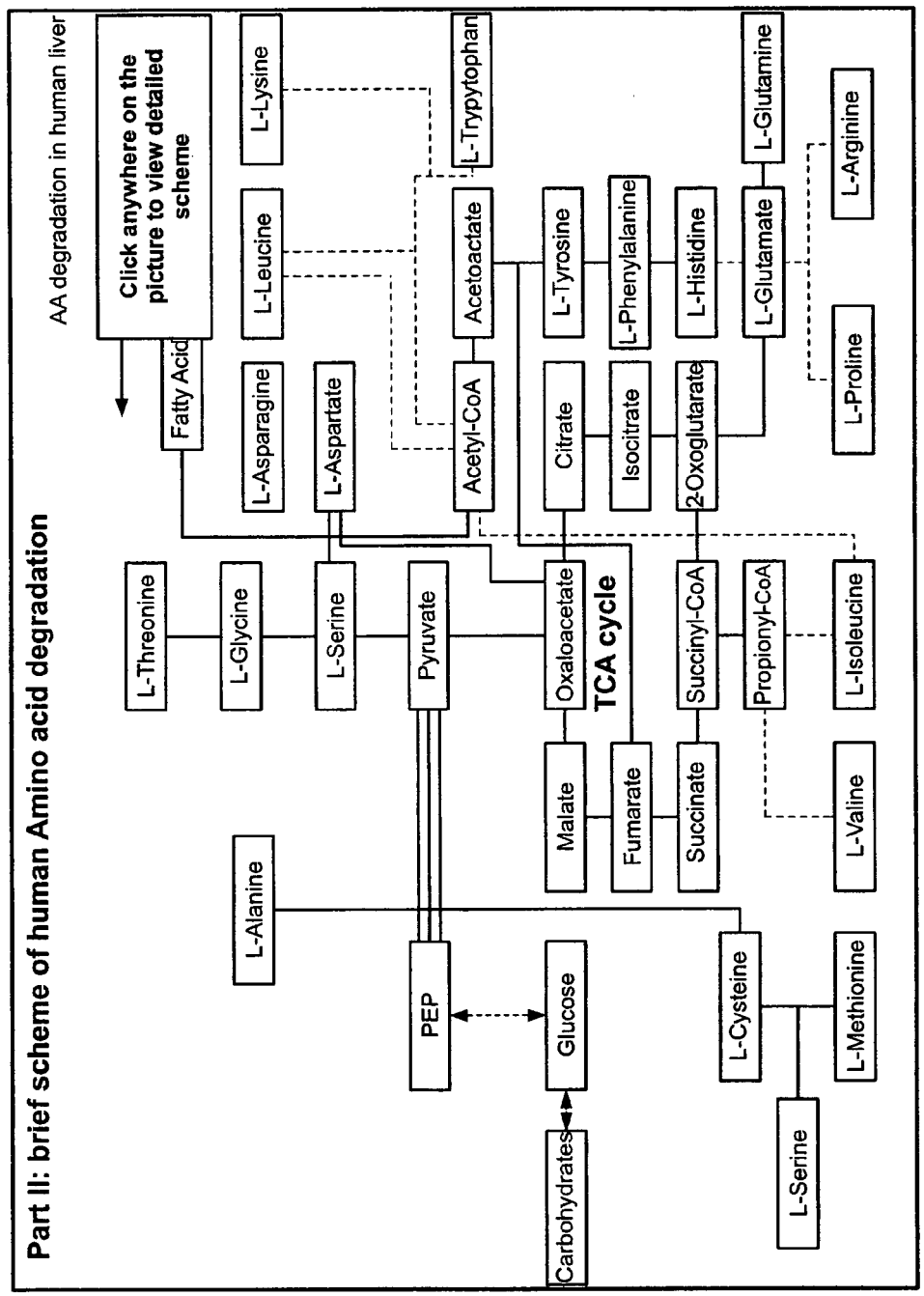
FIG. 5 illustrates a brief scheme of human amino acid degradation.

The technology of the present invention was used to build the System Reconstruction of amino acid metabolism in humans (discussed in greater detail in Example 2), a portion of which is illustrated in FIGS. 4 and 5. The reconstruction consists of two major parts: amino acid biosynthesis (FIG. 4) and amino acid biodegradation (FIG. 5).

The user interface of the reconstruction is an interactive map showing pathways involved in amino acid metabolism. This annotated map of interconnected pathways is a "front end" to the underlying database containing entries into pathways, enzymes, metabolites, genes, and information about human diseases. The entities in the database are preferably linked through the core functional network, enabling a user to identify data linked by functional relationships.

A user can also retrieve information about the involvement of a particular pathway, reaction, or enzyme for a specific disease. Preferably, structured annotations are accessible for the elements of the network (e.g., for pathways, reactions, enzymes, and the like) that specify whether the element is the cause of the disease or a manifestation of the disease (part of the disease fingerprint). In addition, a user is able cross-link among the biochemical fingerprints of different diseases. The information is accessible "on-click" from the corresponding objects on the graphical map.

Figure 6:
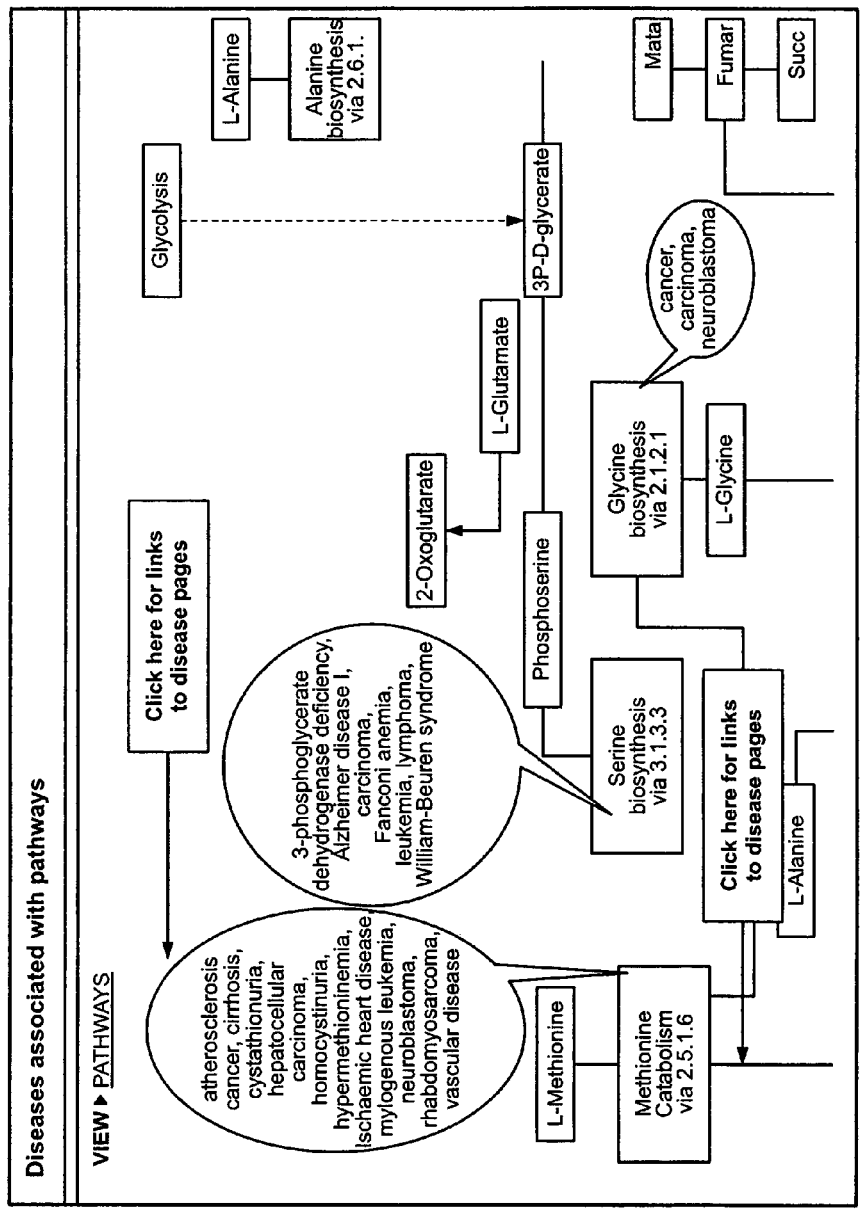
FIG. 6 is an example of a diagram showing diseases associated with pathways.
Figure 7:
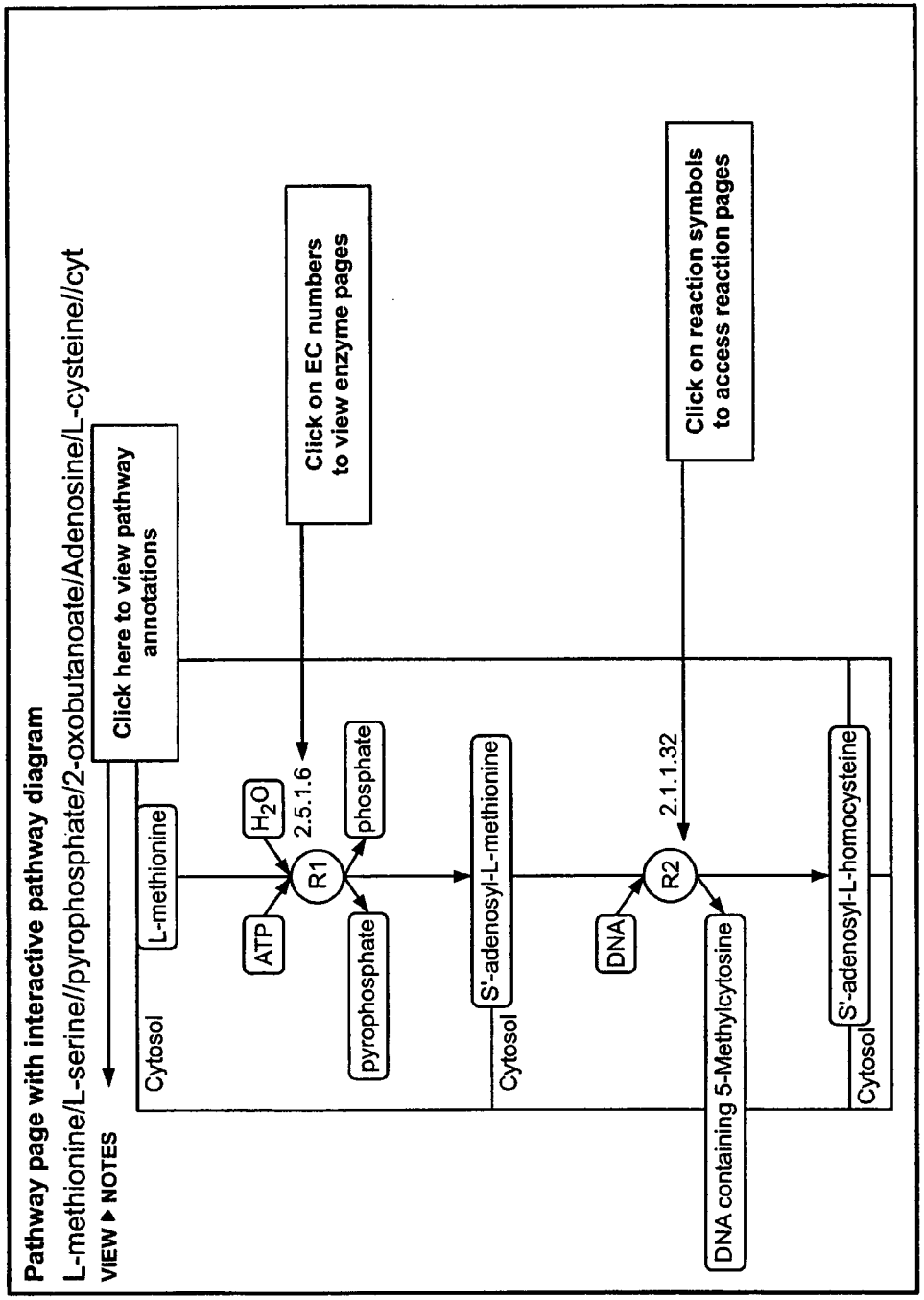
FIG. 7 is an example of a pathway page with an interactive pathway diagram.
Figure 8:
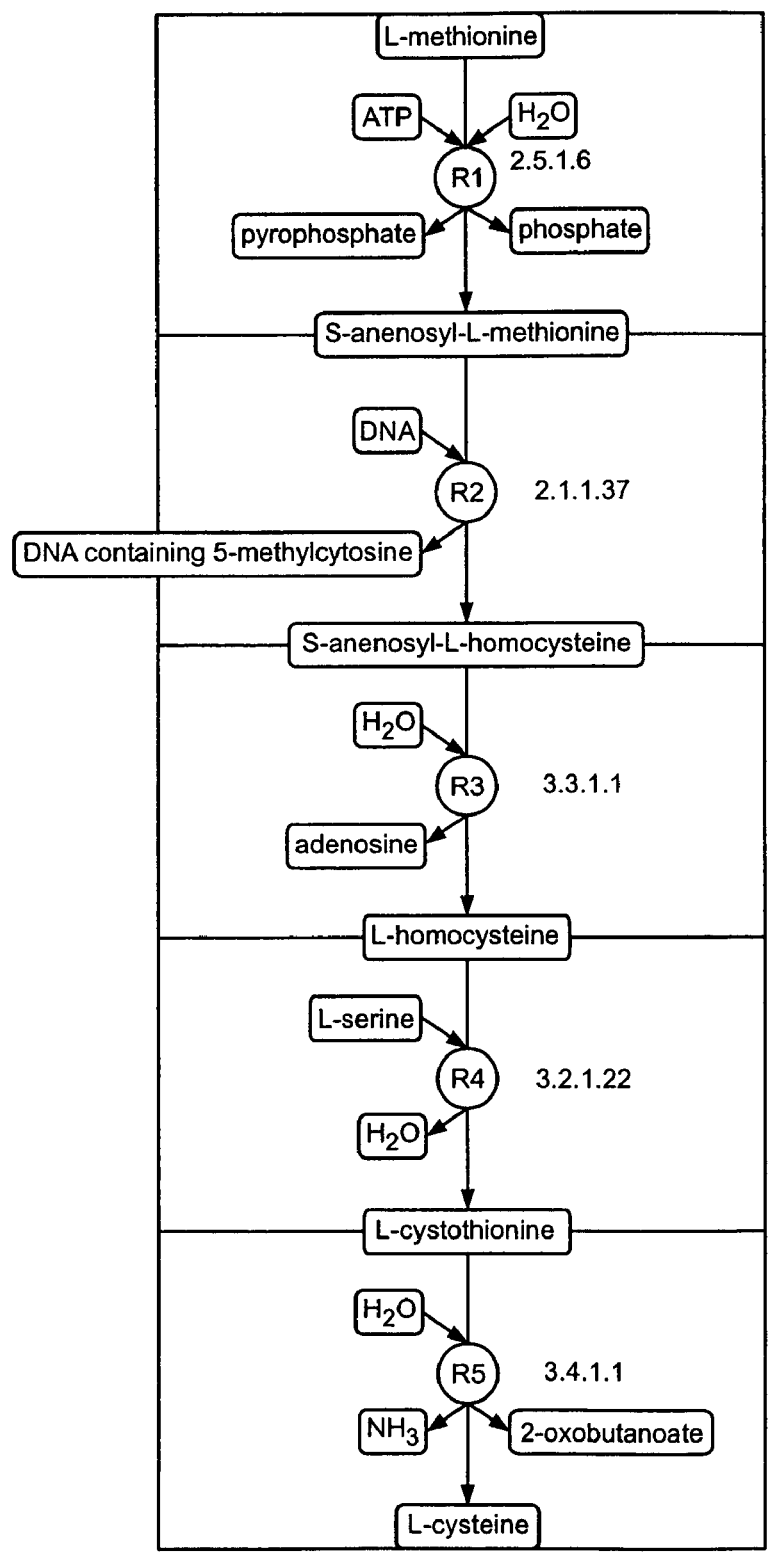
FIG. 8 is an example of a full view of a pathway diagram.

Pathways are interconnected into a network by shared metabolites. By clicking the mouse on a pathway or a component of a pathway, a user can access the pathway page (FIGS. 7 and 8) showing detailed diagrams with all reactions and enzymes. From this page, related pages for enzymes (FIGS. 9A and 9B), reactions (FIG. 10), and genes (FIG. 11) can also be accessed. In addition, pathway notes which describe diseases (FIG. 6) that are linked to the pathway are accessible from this page. An enzyme page enzymes (FIGS. 9A and 9B) contains the enzyme name and its synonyms, links to gene pages for genes related to the enzyme, a list of reactions and pathways in which the enzyme is involved, and notes on the involvement of the enzyme in human diseases.

Figure 13:
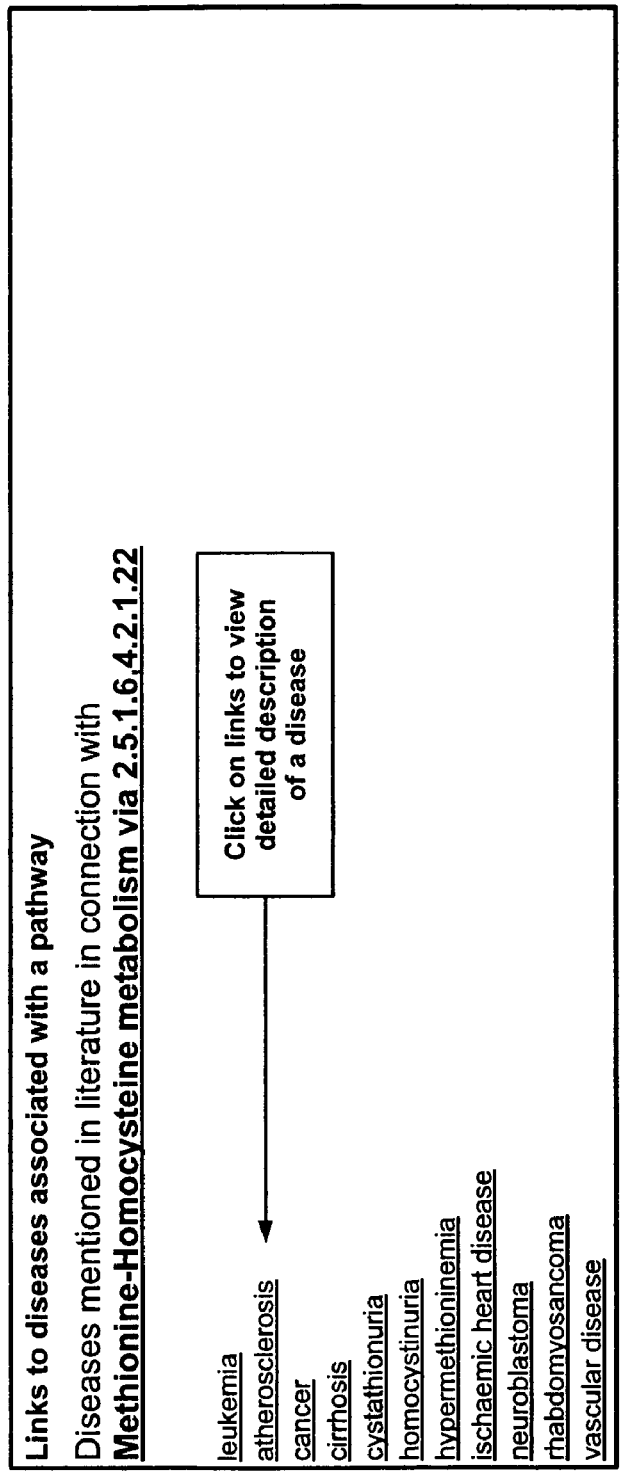
FIG. 13 is an example of a diagram showing links to diseases associated with a pathway.
Figure 14:
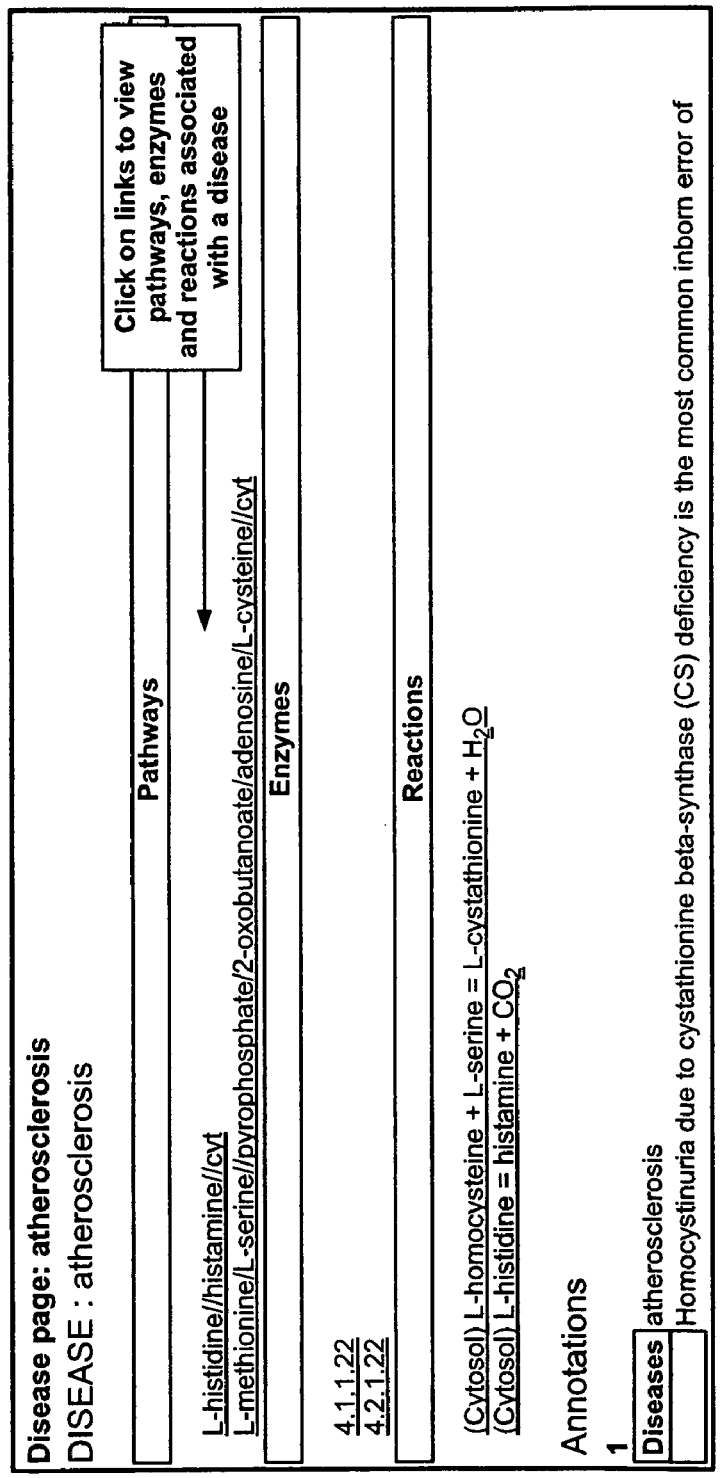
FIG. 14 is an example of a disease page for atherosclerosis.

One feature of the reconstruction is the incorporation of human diseases. By activating a link to diseases, a user can see lists of diseases associated with the pathway (FIG. 13). From these lists, pages for individual diseases (FIG. 14) can also be accessed. These pages contain lists of enzymes, reactions, and pathways that have been linked to a disease. In addition, one can view notes describing various aspects of a disease mechanism, its metabolic causes, and/or its manifestations (FIGS. 15-19).

One aspect of the System Reconstruction technology of the present invention is that it uses organism specific pathways to build maps. This allows the imposition of a condition of self-consistency on the resulting networks. This means that each metabolite should either be essential for the organism (e.g., consumed through food) or there should be a pathway that produces it. In other words, if there is a gap between two nonessential compounds, this implies a lack of knowledge and serves to direct further research. This allows the prediction of the existence of an enzyme function in an organism even if organism-specific genes or proteins have not been identified. For example, when there is a clear gap between two metabolites in the reconstruction that cannot be filled in by any of the described enzymes, it is predicted that there is at least one undescribed enzyme that bridges this gap. In the present reconstruction of amino acid metabolism in humans, several human enzymes were identified that had not been previously identified in the human genome. These enzymes, including amino-carboxymuconate-semialdehyde decarboxylase (EC 4.1.1.45) and imidazolone-5-propionate hydrolase (EC 3.5.2.7), were identified because their functions were required by the logic of the metabolic map. Consequently, human genes for these enzymes were proposed through thorough similarity searches of the human genome and by studying human ESTs.

The self-consistency condition also helps eliminate pathways that might be incorrectly assigned merely on the basis of human enzymes having been identified. One example can be illustrated with phenylalanine biosynthesis. It is well known that humans cannot synthesize this essential amino-acid. However, there is a human enzyme, aspartate transaminase (EC 2.6.1.1), that could potentially synthesize phenylalanine from phenylpyruvate. Simply superimposing the human enzyme onto a general metabolic map would lead to the incorrect conclusion that there is a human pathway for phenylalanine biosynthesis. In contrast, the self-consistent reconstruction of the present invention shows that the absence of phenylpyruvate, the substrate for aspartate transaminase, makes biosynthesis of phenylalanine improbable in humans.

Another important feature of the System Reconstruction technology is its potential to predict novel human pathways that have not yet been discovered. Indeed, only a fraction of human functional pathways have been described experimentally. There are still many unknown regulatory, signaling, and even metabolic pathways. At present, there are about 2,000 identified human enzymes. According to both Celera and the Public Human Genome Project Consortium, about 10% of human genes are involved in metabolism. Therefore, humans may have 3,000-4,000 metabolic enzymes in total. Thus, approximately half of the human metabolic enzymes may still need to be identified. System Reconstruction technology enables the proposal of many of these undiscovered human enzymes in the course of creating functional tissue-specific maps. The architecture of the map, including identified pathways, compounds that have been synthesized by these pathways, as well as additional evidence from literature and biological high-throughput data can point to enzymatic functions that are required for the self-consistency of the model, thus identifying undiscovered enzymes.

Figure 36:
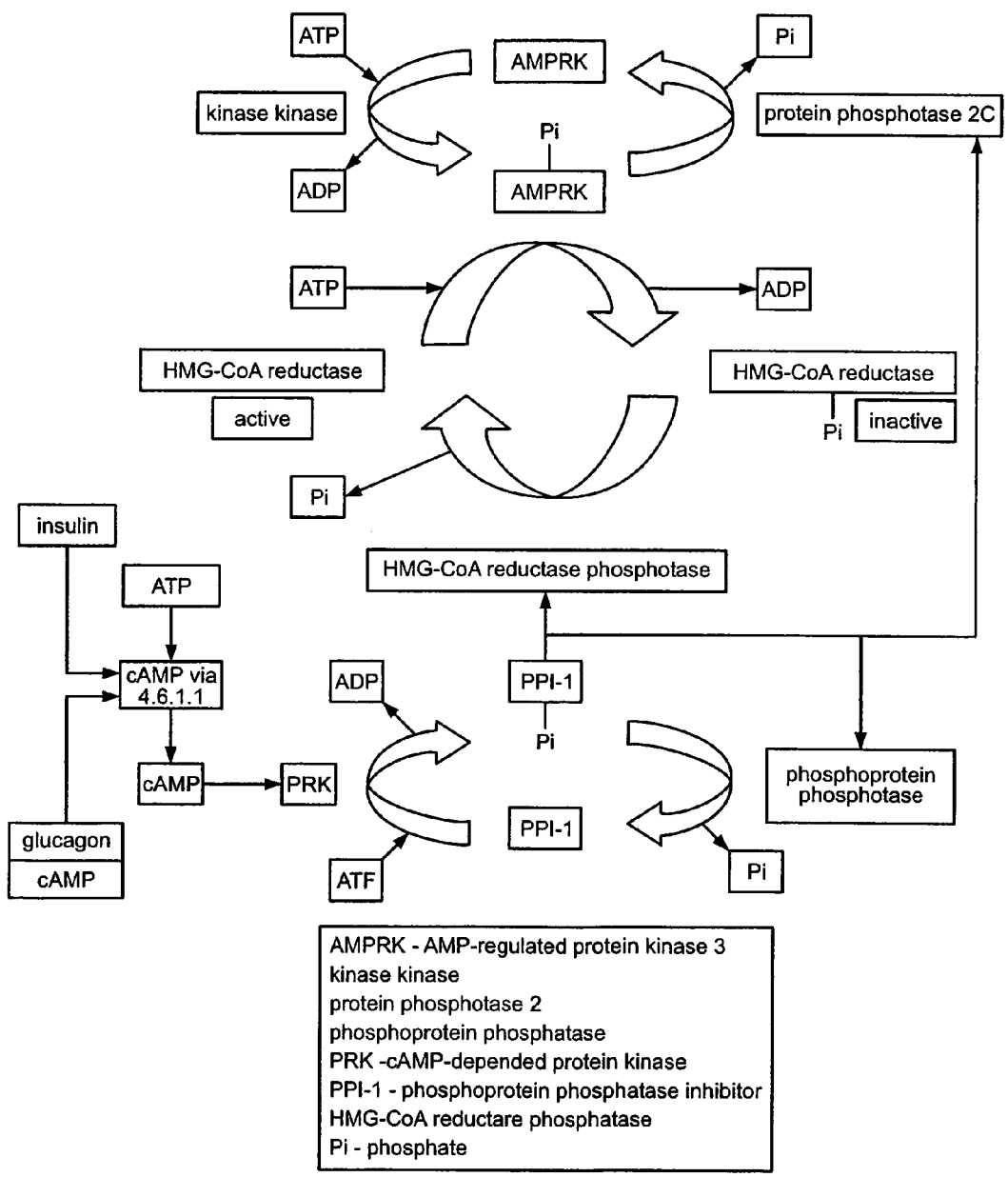
FIG. 36 is a schematic diagram of Post-Translational Modifications.
Figure 37:
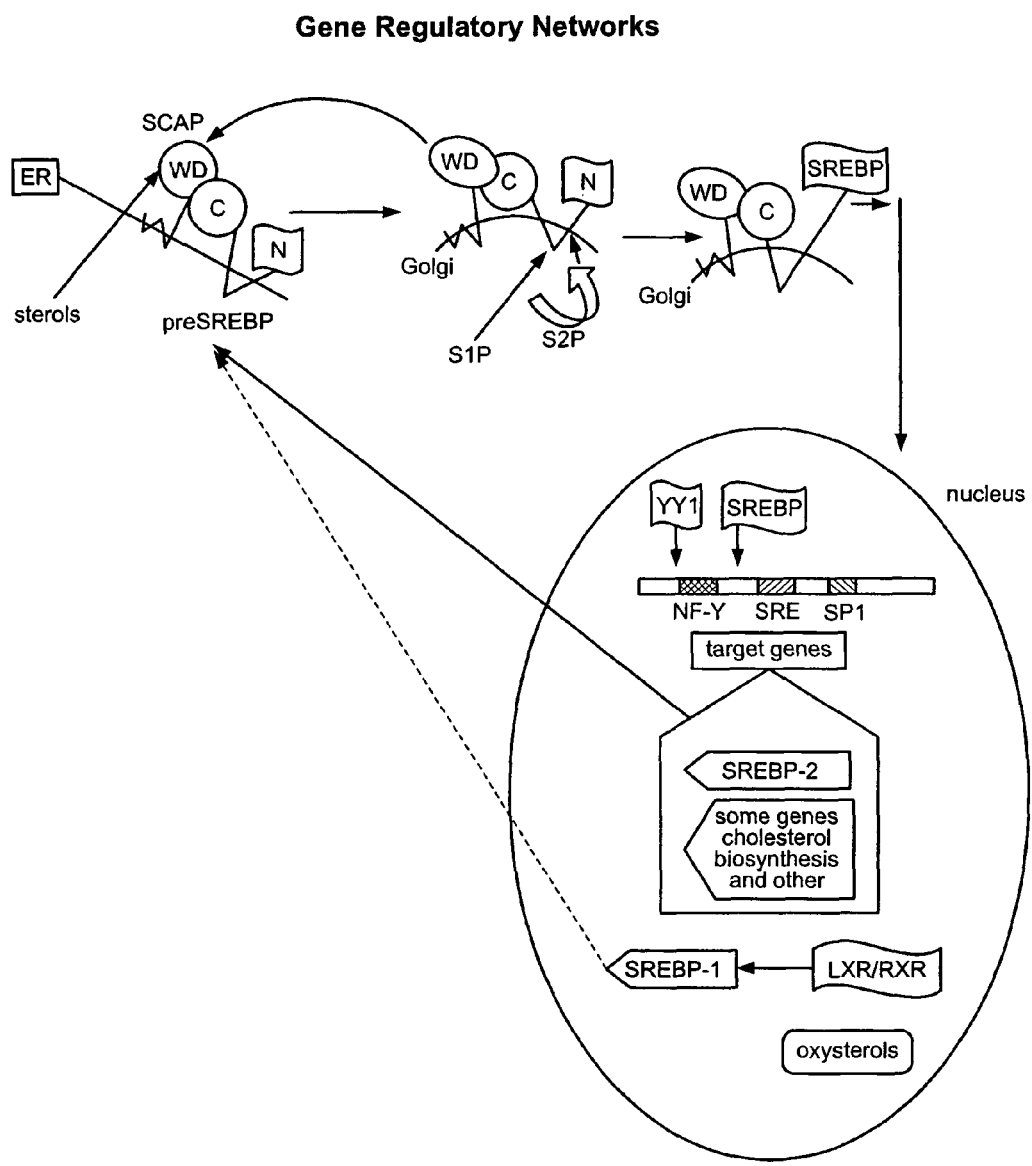
FIG. 37 is a schematic diagram of Gene Regulatory Networks.
Figure 38A:
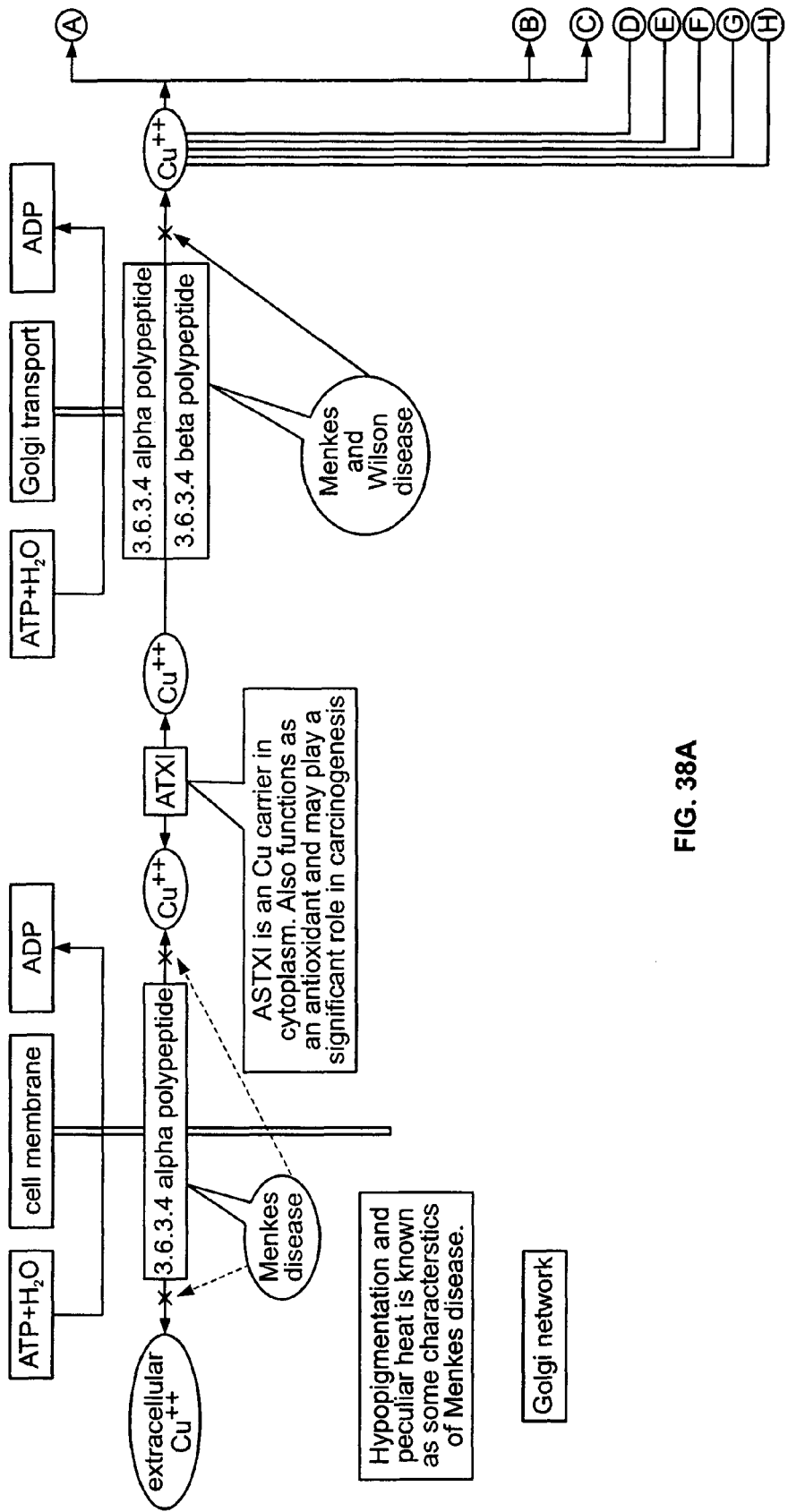
FIG. 38A is a schematic diagram of Signal Transduction Cascades.
Figure 38B:
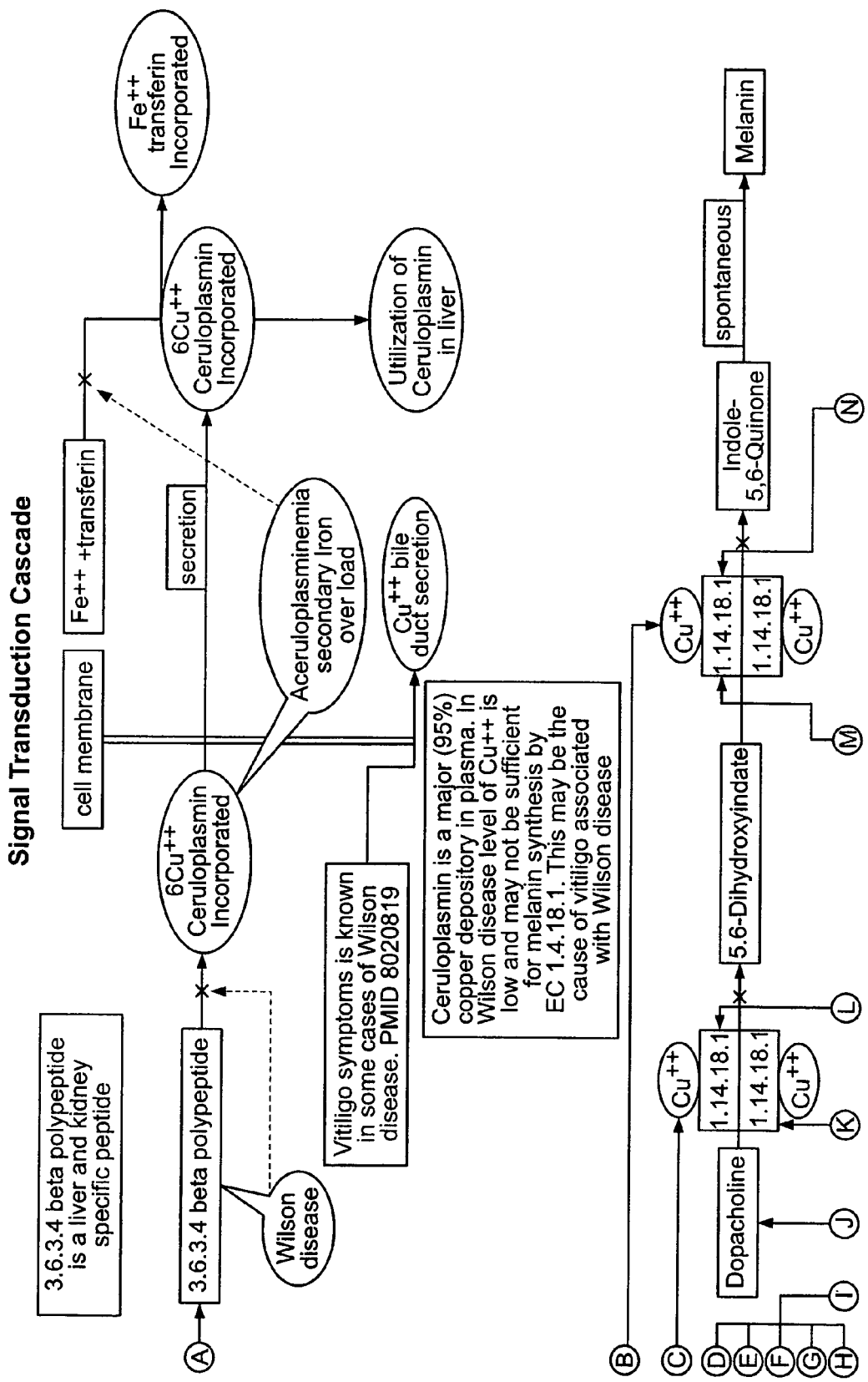
FIG. 38B is a schematic diagram of Signal Transduction Cascades continued from FIG. 38A.
Figure 38C:
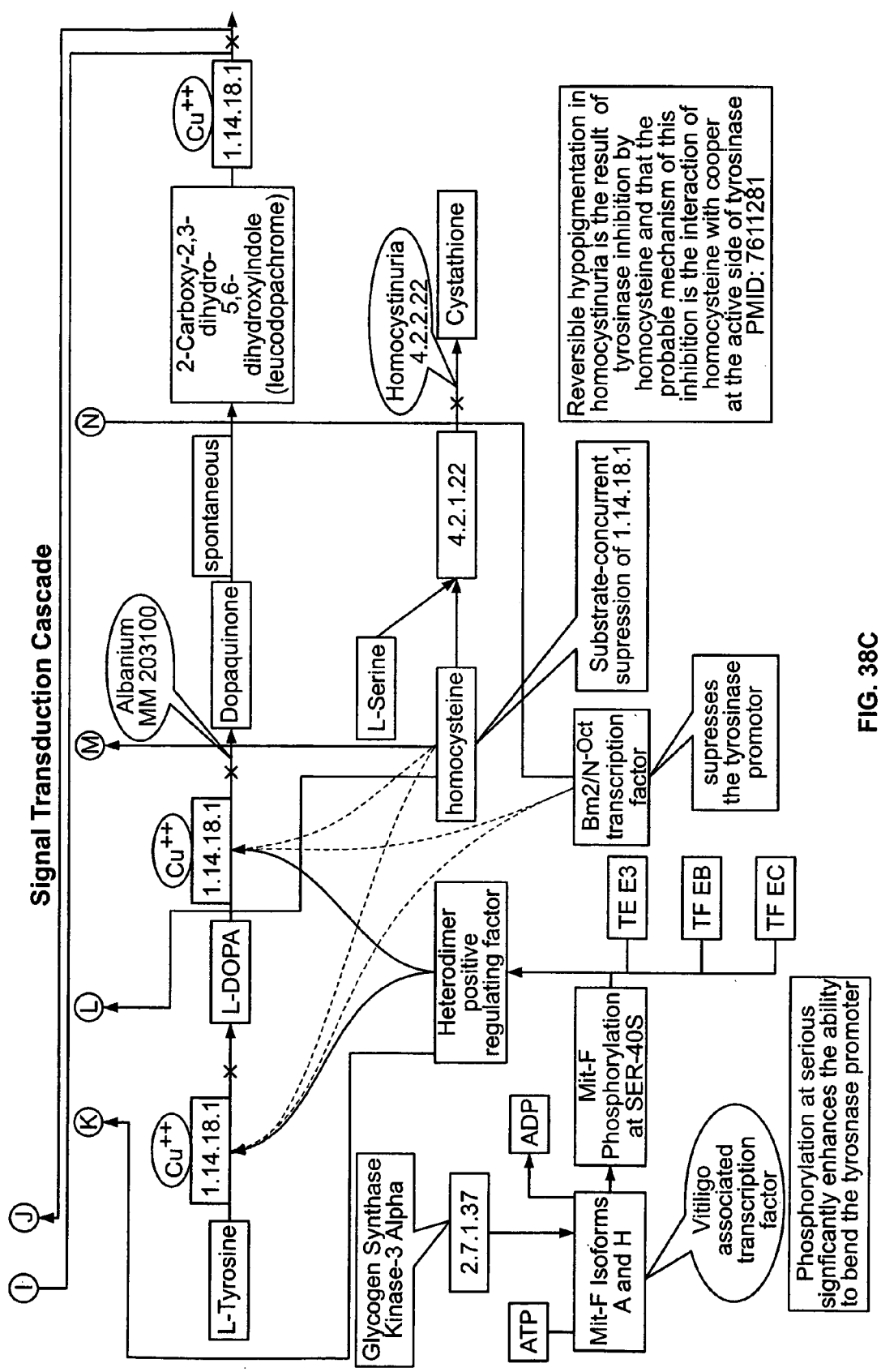
FIG. 38C is a schematic diagram of Signal Transduction Cascades continued from FIGS. 38A and 38B.
Figure 39A:
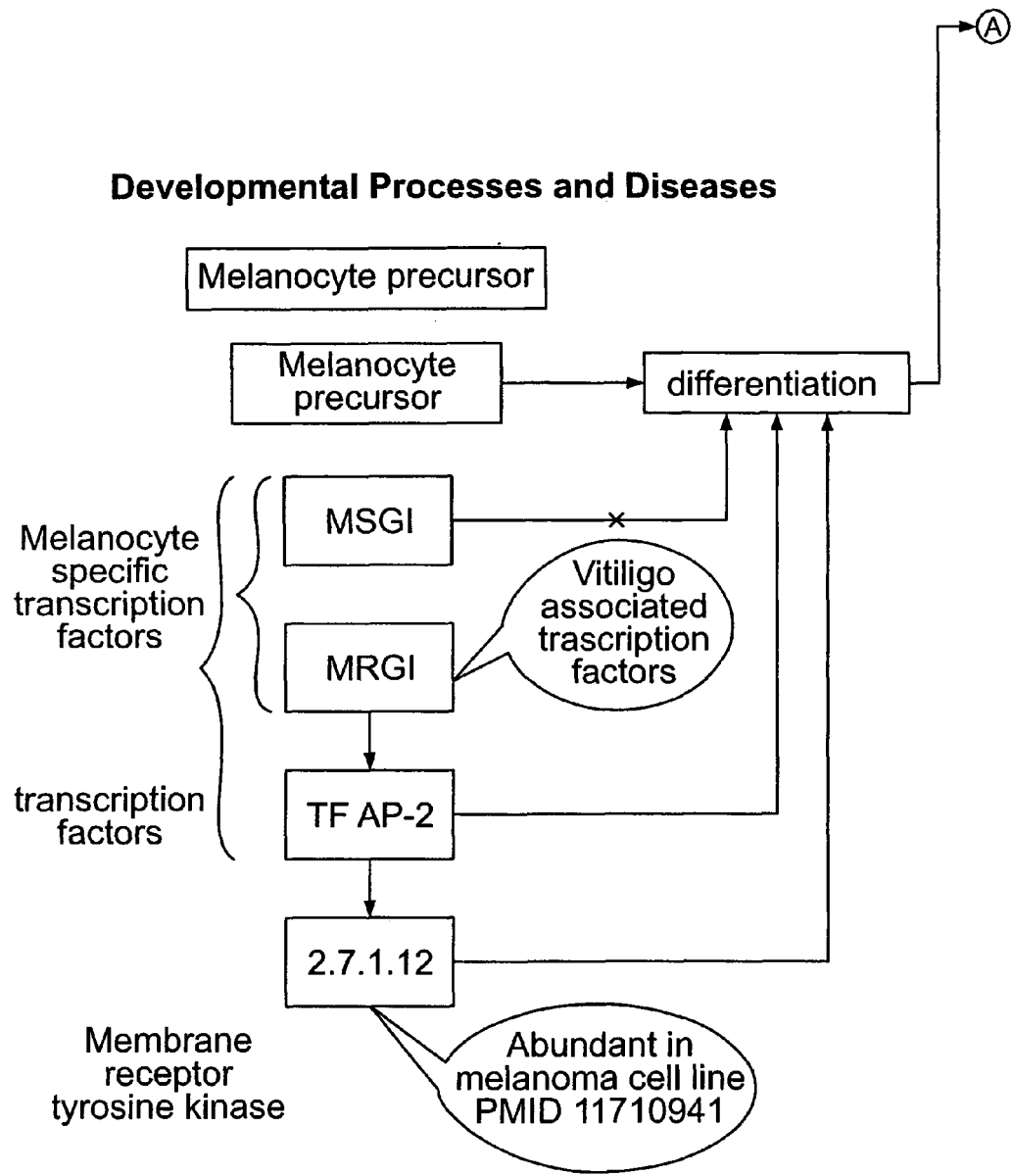
FIG. 39A is a schematic diagram of Developmental Processes and Diseases.
Figure 39B:
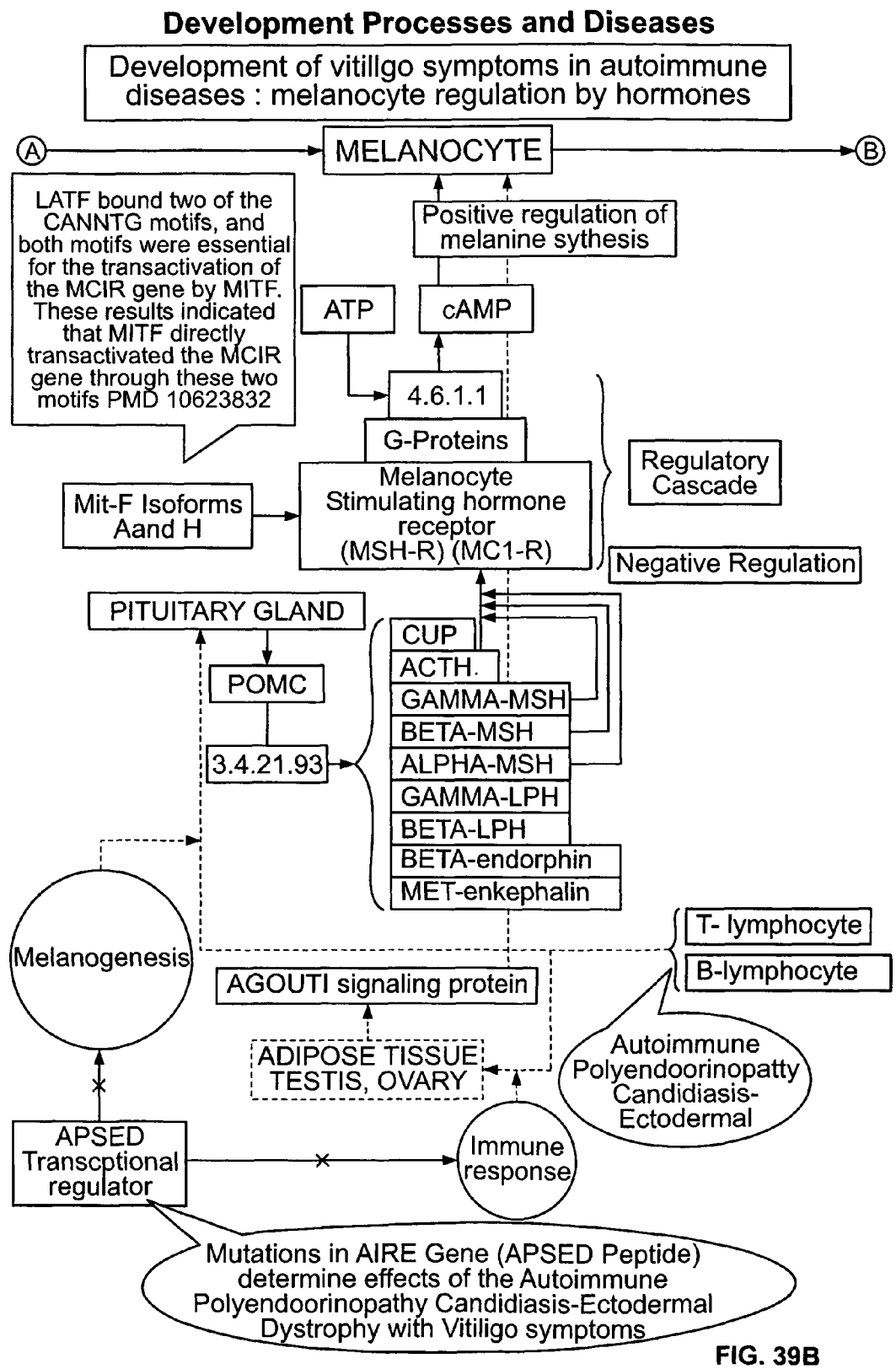
FIG. 39B is a schematic diagram of Developmental Processes and Diseases continued from FIG. 39A.
Figure 39C:
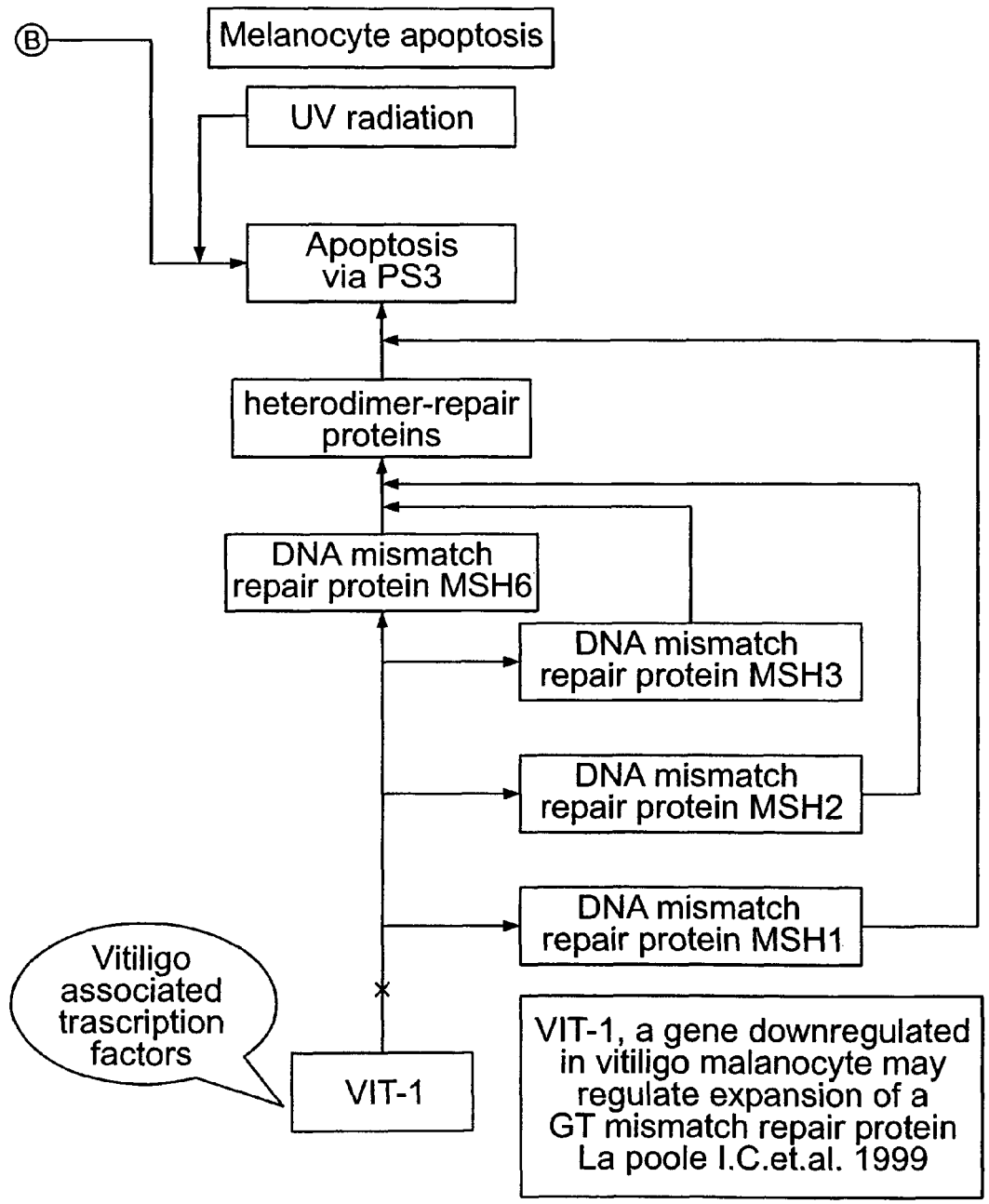
FIG. 39C is a schematic diagram of Developmental Processes and Diseases continued from FIGS. 39A and 39B.

In one preferred embodiment of the present invention, the subject of System Reconstruction is human metabolism. System Reconstruction can be used to study diverse processes including, but not limited to, amino acid metabolism; carbohydrate metabolism; lipid metabolism; hormones; DNA, RNA, and nucleotide metabolism (see, FIG. 37); aromatic compound metabolism; porphyrin metabolism; coenzyme and prosthetic group metabolism; regulation of metabolism (see, FIGS. 33A-C and 34), post-translational modifications (see, FIG. 36); signal transduction (see, FIG. 39A-C); developmental processes (see, FIG. 39A-C); and the like. In addition to studying diverse processes, System Reconstruction is useful for integrating these diverse processes and identifying the relationships and interconnections between them. (See, FIGS. 32-39).

Generally, a formal network would contain reactions that are linked by shared metabolites. In System Reconstruction, pathways are also confirmed through a process of annotation. System Reconstruction allows building of both formal networks, which may contain putative pathways, as well as reconstructed pathways that have been confirmed through a process of annotation.

Figure 2:
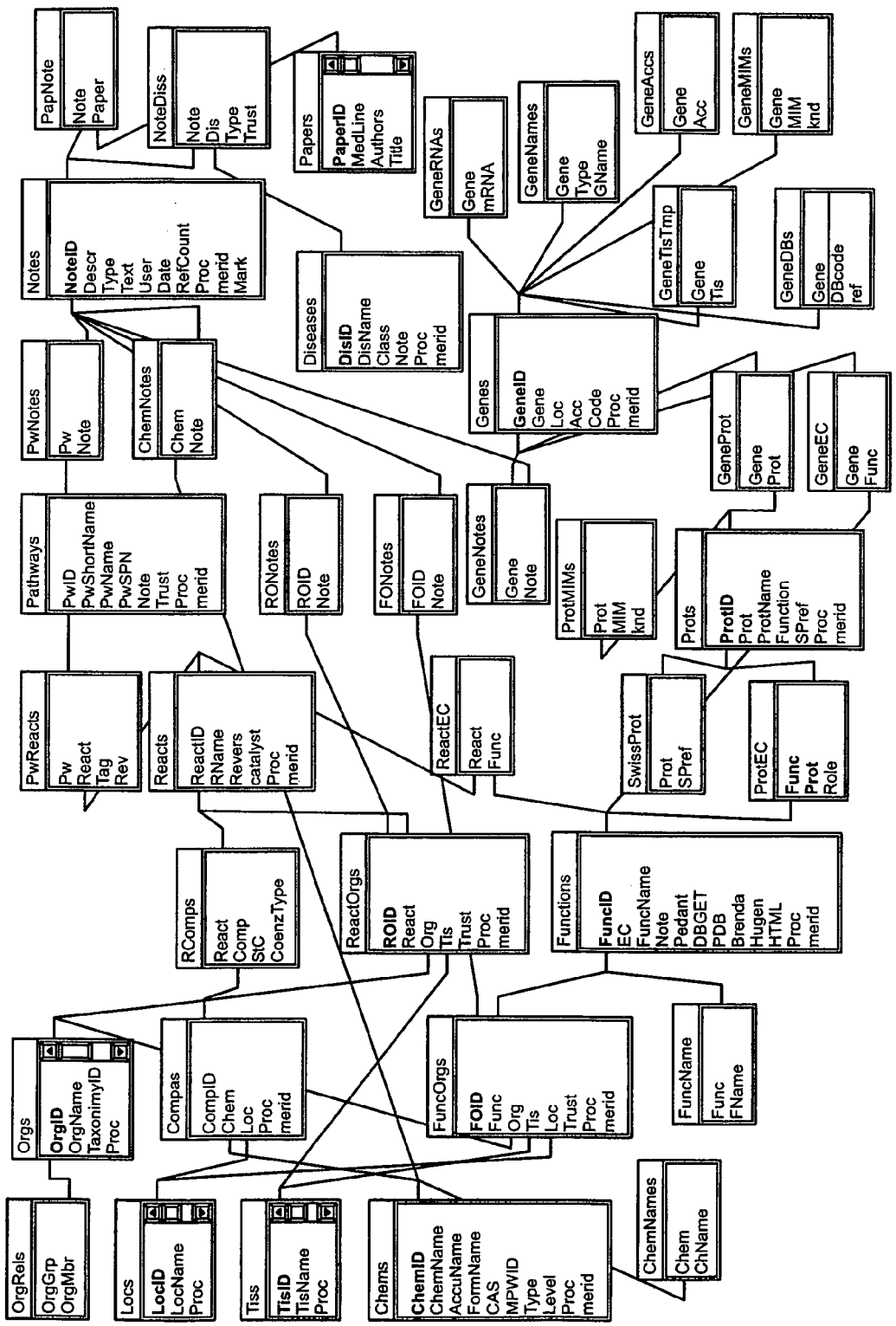
FIG. 2 is a chart illustrating a preferred structure of a System Reconstruction database according to the present invention.

One example of a database architecture according to the present invention is illustrated in FIG. 2. FIG. 2 is a chart showing the some of the types of information that can be made available in a System Reconstruction database as well as some of the interconnections between the various types of information. Example 2 shows how this type of database architecture is reflected in the used interface. The categories of information shown in FIG. 2 relate to an entity in the database and are described briefly as follows:

Orgs, and OrgRels includes information about the organism and its taxonomical classification;

Locs includes information about the subcellular localization;

Tiss includes information about the tissues and organs in which the entity is present;

Chems, and ChemNames includes information about chemical compounds, their names, and synonyms;

Compas includes information about unique combinations such as a chemical and its subcellular localization (for example, glucose in cytoplasm);

Reacts includes information about reactions;

Rcomps includes information about links between the Reacts and Compas categories (for example, a chemical formula or reaction and its subcellular localization);

ReactOrgs includes information about organisms and tissues in which a reaction occurs;

Functions, and FuncNames includes information about enzymes, their EC numbers, their names, and their synonyms;

FuncOrgs includes information about organisms, tissues in which an enzyme is present as well as information about subcellular localizations;

ReactEC includes information about links between enzymes and reactions, showing which enzyme(s) catalyze a given reaction;

Pathways includes information about pathways, or sequences of several reactions;

PwReacts includes information about the reaction composition of a pathway;

Prots includes information about proteins, including the name and function of the protein;

ProtEC includes information about which human proteins correspond to a given function (EC number);

SwissProt, and ProtMIMs provide links to external protein databases;

Genes, and GeneNames include information about genes, their names, and their functions;

GeneProts, and GeneEC includes information about links between genes, proteins and EC numbers;

GeneRNAs, GeneDBs, GeneMIMs, and GeneAccs—provide links to external genetic databases;

GeneTisTmp includes information about tissues and EST sources for a gene;

PwNotes, ChemNotes, RONotes, FONotes, and GeneNotes provide links between notes (annotations), pathways, Chems, Reactorgs, Funcorgs, and Genes;

Notes includes information about notes and annotations;

PapNote, and Papers provide references for each note;

NoteDiss, and Diseases include information about how diseases are linked to a note, for example, whether a certain entity is thought to be a cause or manifestation of a disease, or is hypothesized to be involved in a disease.

The following examples describe and illustrate the processes and products of the present invention. These examples are intended to be merely illustrative of the present invention, and not limiting thereof in either scope or spirit. Those skilled in the art will readily understand that variations of the materials, conditions, and processes described in these examples can be used. All references cited herein are incorporated by reference.

EXAMPLE 1

System Reconstruction of *Emericella nidulans*

This example presents the first study of metabolic reconstruction of a eukaryotic organism based solely on Expressed Sequence Tag (EST) data. As illustrated in the present example, the process of the present invention can be used to study metabolism, not just in humans, but in any species. This study was performed within the framework of the WIT 2 system, a WEB-based environment for comparative analysis of genomes, publicly available at the University of Oklahoma's Advanced Center for Genome Technology. See, Overbeek et al., WIT: integrated system for high-throughput genome sequence analysis and metabolic reconstruction, Nucleic Acids Res. 2000 Jan. 1; 28(1):123-5 (PMID: 10592199). The WIT Project was instituted to develop a framework for the comparative analysis of genomic sequence data, focusing largely on the development of metabolic models for sequenced organisms.

*Emericella nidulans* (former *Aspergillus nidulans*) was chosen as a model organism for this work. *Emericella nidulans* has been a classical genetic organism for more than fifty years. Its unique metabolism has been extensively studied, especially with regard to carbon compounds. Carbon and alcohol metabolism, nitrogen assimilation, acetamide and proline utilization, amino acid metabolism, sulfur metabolism, and penicillin and sterigmatocystin biosynthesis are the best characterized metabolic systems in *E. nidulans*. Gene expression and regulation have also been studied extensively in *E. nidulans*. There are some fairly well understood systems, such as nitrogen metabolite repression, carbon catabolite repression, regulation of acetamide utilization, regulation of purine degradation, regulation of metabolic flux in the quinate and shikimate pathways, and regulation of gene expression by pH, oxygen and phosphorus. Recently, significant progress has been made towards understanding genetic regulation of reproduction and development in *E. nidulans*. See, Adams et al., Coordinate control of secondary metabolite production and asexual sporulation in *Aspergillus nidulans*, Curr. Opin. Microbiol. 1998 December;1(6):674-7 (PMID: 10066549); and Adams et al., Asexual sporulation in *Aspergillus nidulans*, Microbiol. Mol. Biol. Rev. 1998 March;62(1):35-54 (PMID: 9529886). Moreover, *Emericella* belongs to a family of industrially important fungi, some of whose members are common human opportunistic pathogens, and all of which are able to produce penicillin and carcinogenic toxins (aflatoxin, sterigmatocystin, etc.). The genome size of *E. nidulans* is about 30 Mb. This organism has a typical ascomycetes life cycle, which includes a vegetative stage and three reproductive cycles: sexual, asexual, and parasexual.

EST data for *Emericella nidulans* and *Neurospora crassa* were provided by the Oklahoma University. Unigene databases for both organisms were created by multiple sequence alignments of different ESTs which were believed to correspond to the same actual gene, providing a more accurate and longer version of the gene sequence. 4155 "unigene ESTS" were provided for *Emericella nidulans* (abbreviated EN in Table 1) and 633 "unigene ESTs" were provided for *Neurospora crassa* (abbreviated NC in Table 1).

Using these unigene entries, similarities to known protein sequences were computed using blastx and by comparison to other EST sequences using blastn. The results are summarized in Table 1. The numbers in Table 1 represent the percentage of sequences from E. nidulans and N. crassa that show similarity to sequences from each of the other organisms listed. For example, 29.2% of E. nidulans sequences and 34.9% of N. crassa sequences show similarity to the yeast sequence.

TABLE 1

|  | Hits | | Hits with function | |
| --- | --- | --- | --- | --- |
|  | EN | NC | EN | NC |
| Yeast | 0.292 | 0.349 | 0.205 | 0.273 |
| C. elegans | 0.162 | 0.238 | 0.157 | 0.222 |
| N. crassa | 0.067 | N/A | 0.063 | N/A |
| E. nidulans | N/A | 0.202 | N/A | 0.192 |
| Any eukaryote | 0.457 | 0.597 | 0.408 | 0.557 |
| Any bacteria | 0.157 | 0.306 | 0.171 | 0.276 |
| Any archaea | 0.059 | 0.145 | 0.054 | 0.140 |
| Anything | 0.484 | 0.631 | 0.432 | 0.586 |

About 40-60% of the sequences fail to show similarity to any protein in the nonredundant protein database with a cutoff of 1.0e, which is quite strict. When the cutoff was set at 1.0e-2, an additional 5% of the ESTs showed recognizable similarity. The fraction of hits against proteins with known function in Emericella nidulans is slightly lower than the percentages that are seen with complete chromosomal sequences for the ORFs, which is about 55-60% at this time). EST data, and even unigene EST data, is made up of relatively short sections of genes that include frameshifts. Without the frameshifts, blastx (or FastA) would produce excellent results. The recognizable similarities would certainly go up in the cases involving frameshifts if they could be corrected or if approximate translations estimating the position of the frameshift could be produced. It may be possible to achieve this type of result if ESTs from a closely related organism were available.

The goal of the instant example is to produce an accurate System Reconstruction for Emericella nidulans based on the available EST data. System Reconstruction generally involves two steps. First, assignment of a function to each unigene number is made. Second, a set of metabolic pathways specific for the organism is identified. Since each asserted pathway is composed of a set of functional roles (i.e., enzymes), the unigene entries, with their appropriate functions and corresponding EC numbers, were associated with each of the asserted pathways. The comparative value of the reconstruction from EST data versus reconstruction based on genomic data is summarized in Table 2 below.

TABLE 2

| Organism | S. cerevisiae Genomic data | E. nidulans EST data |
| --- | --- | --- |
| Genome size | 12.01 Mb | about 30 Mb |
| Available ORFs | 6,261 ORFs | 4,472 unigene ESTs |
| % of the genome | 100% | 15% |
| Functions assigned | 3,119 ORFs | 2,826 ORFs |
| Pathways identified | 462 | 602 |

Assignments were made to about 2,800 of the ESTs, and then development of an emerging model of the metabolism of E. nidulans began. An extensive literature search for E. nidulans has been performed. The search focused on known metabolic pathways of this organism, as well as on gene regulation and physiology of filamentous fungi. Almost every pathway asserted for E. nidulans has a corresponding reference included in the annotation. The current reconstruction is composed of more than 600 asserted pathways which connect to about 500 specific ESTs. Many pathways are composed of a single reaction, and many others are known to exist biochemically but specific ESTs corresponding to the appropriate functional roles could not be identified. Thus, the collection of assigned functions and asserted pathways represents a model of the metabolism of E. nidulans. This model can be integrated with the growing body of both genetic sequence data and available biochemical characterizations. Such integration forms the basis for a continuing analysis of the organism. The current status of system reconstruction for both S. cerevisiae and E. nidulans is summarized in Table 3, below. Some of the asserted pathways have broken down into categories. The numbers in Table 3 indicate where the analysis is relatively complete and where it is sparse or lacking altogether. Some of these pathways are single reactions that may have similar forms in different cell states.

TABLE 3

|  | Number of pathways asserted | |
| --- | --- | --- |
| Metabolic category | Yeast | E. nidulans |
| Amino Acid Metabolism | 139 | 162 |
| Aromatic Hydrocarbons | 1 | 8 |
| Carbohydrate Metabolism | 97 | 147 |
| Coenzymes and Vitamins | 23 | 23 |
| Electron transport | 10 | 10 |
| Lipid Metabolism | 34 | 36 |
| Membrane Transport | 14 | 22 |
| Oxygen and radicals | 6 | 8 |
| Nitrogen Metabolism | 0 | 1 |
| Nucleic Acid Metabolism | 17 | 17 |
| One-carbon metabolism | 3 | 3 |
| Phosphate Metabolism | 7 | 7 |
| Protein Metabolism | 23 | 25 |
| Purine Metabolism | 46 | 51 |
| Pyrimidine Metabolism | 35 | 36 |
| Sulfur Metabolism | 4 | 4 |
| Signal Transduction | 1 | 1 |

As the System Reconstruction of E. nidulans for a given number of unigene entries was completed, a visual outline for major parts of metabolism was created. Such schemes not only provide descriptive overviews of certain parts of metabolism, but also reflect the expression patterns specific for a given EST library. The expression patterns become evident when the representation of enzymes in pathways is compared with different sources of expression data, independent from EST data. The expression pattern of identified genes in the reconstruction strongly correlates with data present in the literature, further validating the method of System Reconstruction. For example, one of the most important secondary metabolic pathways, the sterigmatocystin biosynthetic pathway, composed of at least 29 enzymatic activities, is developmentally regulated. A positive correlation between both asexual and sexual sporulation and synthesis of the mycotoxin has been documented (See, Adams et al., Coordinate control of secondary metabolite production and asexual sporulation in Aspergillus nidulans, Curr. Opin. Microbiol. 1998 December;1(6):674-7 (PMID: 10066549); Adams et al., Asexual sporulation in Aspergillus nidulans, Microbiol. Mol. Biol. Rev. 1998 March;62(1):35-54 (PMID: 9529886); and Guzman-de-Pena et al., Correlation between the regulation of sterigmatocystin biosynthesis and asexual and sexual sporulation in Emericella nidulans, Antonie Van Leeuwenhoek, 1998 February;73(2):199-205 (PMID: 9717578)). In the present study, a cDNA library was constructed from *E. nidulans*, strain FGSC A26 (veA1, bio), which had undergone development for 24 hours on a solid surface with an air interface and, therefore, contained cDNAs from both vegetative mycelial cells and cells involved in asexual reproduction. Indeed, unigene numbers for all 29 genes in the pathway have been identified, and most of them had several candidates for the same gene. Another example is the penicillin biosynthetic pathway which consists of only 3 enzymes: DELTA-(L-ALPHA-AMINOADIPYL)-L-CYS-TEINYL-D-VALINE SYNTHETASE (acvA), ISOPENI-CILLIN N SYNTHETASE (ipnA), and ACYL-COENZYME A:6-AMINOPENICILLANIC-ACID-ACYLTRANS-FERASE (aatA). Expression of both acvA and aatA is slightly repressed by glucose in fermentation medium. Brakhage, Molecular regulation of beta-lactam biosynthesis in filamentous fungi, Microbiol. Mol. Biol. Rev., 1998 September;62(3):547-85 (PMID: 9729600). Consistent with literature data, there are no unigene candidates for acvA, one for aatA, and two for ipnA.

The reconstruction of *E. nidulans* metabolism illustrates the use of System Reconstruction from EST data. In fact, alterations to WIT required to support an analysis based upon both EST and chromosomal sequence data have been made. The outcome represents an initial effort to encode the known metabolism of *E. nidulans* and to relate the analysis to actual sequence data (in this case largely ESTs). Such an effort lays the foundation for an ongoing analysis of the genome and embeds the analysis in a framework that supports comparative analysis between organisms.

EXAMPLE 2

System Reconstruction of Amino Acid Metabolism

Figure 20A:
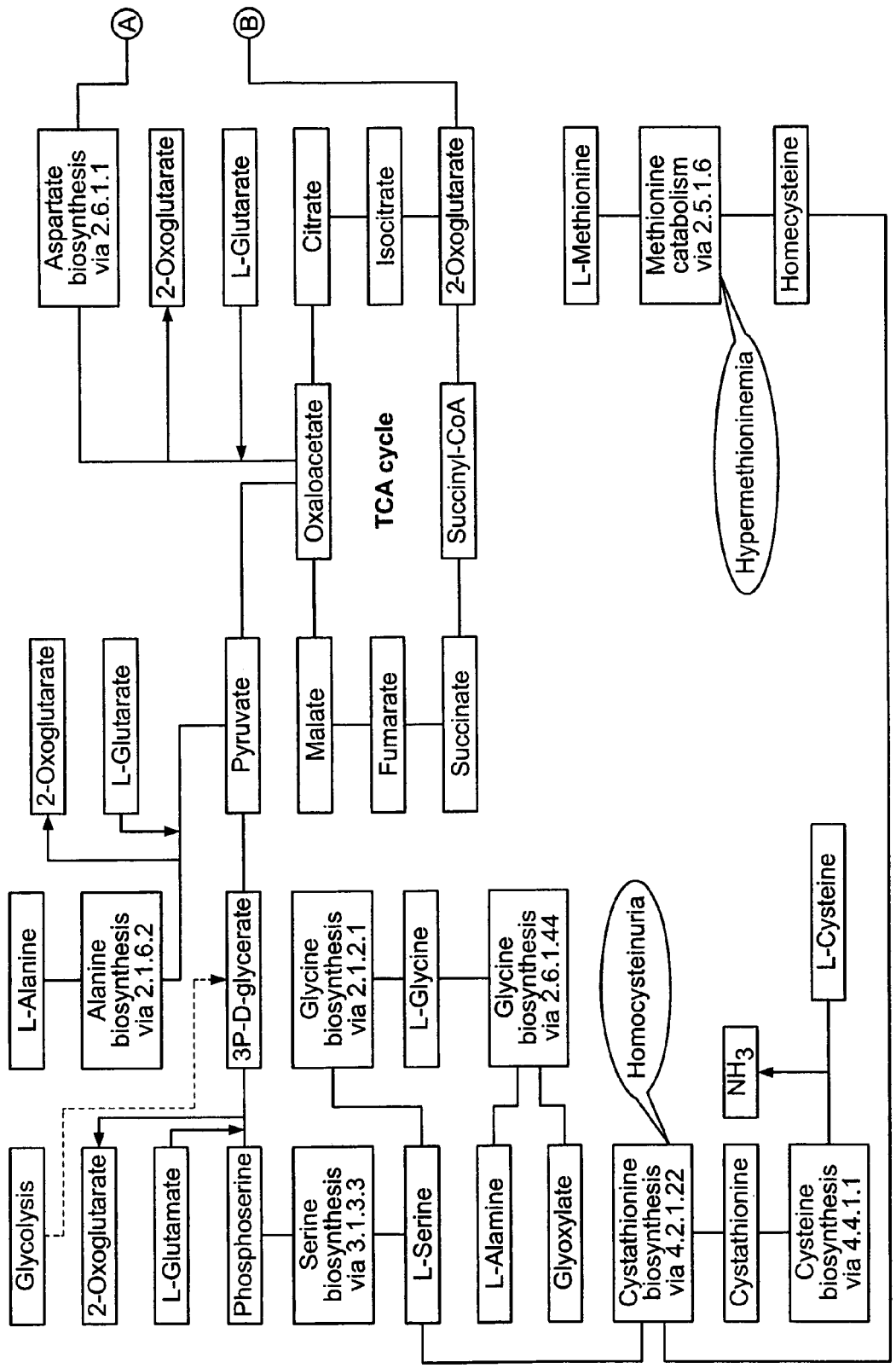
FIG. 20A is an illustration of a TCA cycle map.
Figure 20B:
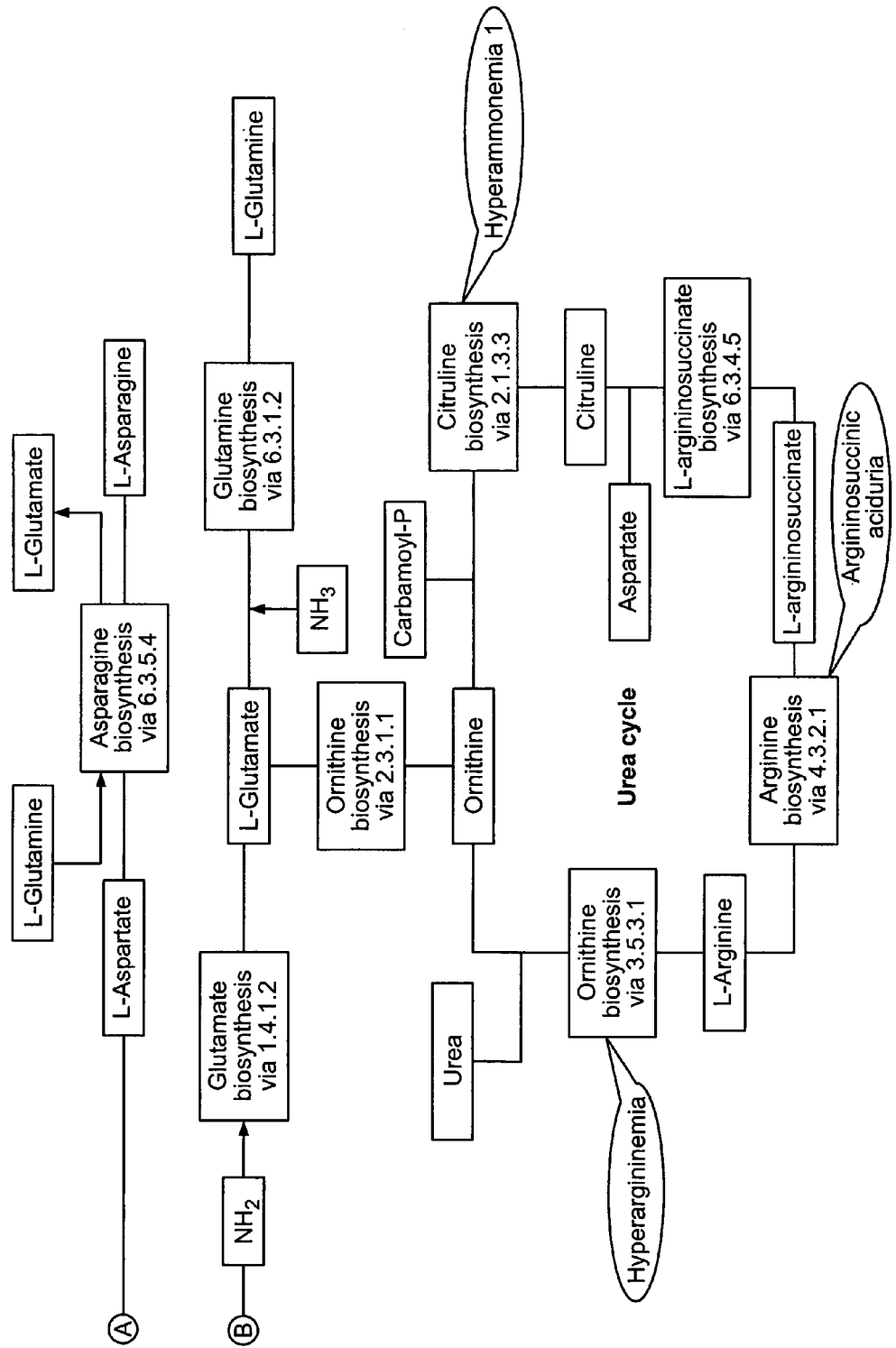
FIG. 20B is an illustration showing an enlarged view of a portion of the TCA cycle map in FIG. 20A.

The System Reconstruction method was used to analyze amino acid metabolism in humans. A portion of the reconstructed map showing the TCA cycle is shown in FIG. 20A-B. System Reconstruction utilizes various types of information for different data fields. Examples of the types of data gathered, analyzed, and integrated are discussed below.

For each of the enzymes, the following data is collected: systematic name and synonyms; EC number (if assigned); a spectrum of substrates and products, including not only specific compounds, but also classes of compounds; known inhibitors and activators; kinetic data, including constants such as $K_M$ and $V_{max}$ for the enzyme or semi-quantitative data on reaction time-scales; and bibliographic references.

The database of amino acid metabolism includes about 150 reactions and pathways described in biomedical literature as involved in biosynthesis and degradation of amino acids. These are reactions and pathways that have been identified experimentally. The following types of information are collected for each reaction or pathway: participating compounds and their roles; a spectrum of enzymes catalyzing the reactions in the pathway, indicating enzymes whose involvement has been identified experimentally in vivo and, those that could participate in the pathways based on their ability to catalyze pathway's reactions; localization and compartmentalization of components; kinetic data, whenever available; and bibliographic references.

For intermediate compounds that occur in the collected pathways and reactions, the following types of data are collected: systematic name of the compound and synonyms; compound classification and compound major structural and functional groups; the endogenous status of the compound in human metabolism (whether the compound occurs as a natural intermediate in human metabolism); thermodynamic data such as free energy, enthalpy and entropy of formation; and bibliographic references. Thermodynamic data are used in combination with metabolic profiles to evaluate the plausibility of the proposed novel pathways.

The first step in building functional models is to link the collected pathways into metabolic networks. There are different types of molecules as well as different types of interactions between biological molecules, and these are indicated through different types of links. Such links are implicitly contained in the database. Indeed, whenever two pathway records share a common intermediate, or an intermediate in one pathway occurs as a regulatory factor in a record for the enzyme from another pathway, it implies a link between these two pathways. Further computations would be facilitated, however, if such links translate into explicit relations among pathways. To this end, a set of special database queries have been developed that extract such relationships and generate tables to describe such links explicitly. These tables constitute a computer representation of a biochemical network that forms a skeleton of the System Reconstruction Model. Unlike the assembled or statistically inferred networks used in many studies, the System Reconstruction Model is built from experimentally verified pathways that may be thought of as identified routes on a biochemical network. It is important to note that only a small fraction of all possible reaction sequences are realizable as functional pathways in any given organism. The types of relationships included in the network may include, for example, the following: pathways linked by shared substrates and/or products; activation of an enzyme by the intermediate metabolite; inhibition of an enzyme by the intermediate metabolite; metabolites that lead to the induction of expression of an enzyme-related gene; metabolites that lead to the suppression of the expression of a gene; and regulation of a transporter or channel by an intermediary metabolite. As the data are collected, other import links may become evident and can be included in the model.

The next step involves converting the network of pathways into a System Model. A network of pathways is only a skeleton on which other data can be assembled. Data integration is accomplished by a specially developed procedure called Structured Annotation. In the course of this procedure, links are established between particular elements in a pathway network. Elements include, for example, pathways, enzymes, metabolites, and the like. This procedure is practically achieved by filling in the annotation tables associated with each element. There are three major categories of data that are integrated into the model at this stage: function-related information; molecular data; and clinical manifestations of human diseases.

Function-related information for pathways and reactions includes functional roles in the human body. These roles may be represented as the catabolism or biosynthesis of certain important molecules, cell energetics, activation, inhibition of various cellular processes, and the like. Functional assignments are not exhaustive, as they have likely resulted from the sets of experiments focused on the specific function. Taken together and integrated within the network of pathways, however, they represent a useful picture of biological functionality and its underlying mechanisms. The types of information used include organ and tissue localization of the pathway element; intracellular localization and/or compartmentalization; the existence and subcellular localization of the element in other organisms; and references to the primary information source.

Molecular data may include, for example, sequence data, such as genes, ORFs, and Unigene clusters that are associated with enzymes; conditional expression information for an enzyme; genetic polymorphisms of an enzyme and the impact of such polymorphisms on its properties; references to the primary information source; cross-references to records in public genomic databases such as Genebank and TrEMBL; and the like.

Clinical manifestations may include, for example, connection of the element with a disorder (cause, manifestation, and the like); references to the primary information source; and the like. One feature of the model is the incorporation of clinical manifestations (traits) and the ability to view and analyze these data types within the framework of other data integrated into the model. Some clinical traits are directly linked to alteration of a certain biological functions while others are associated with particular genes, proteins, or compounds. The latter are often statistical correlations (e.g., a mutation in a gene correlates with predisposition to a certain disease). In the System Reconstruction Model, biological functions, molecular data, and clinical traits are all linked to a network of pathways. Such a representation allows for the elucidation of the biochemical mechanisms that underlie specific clinical observations.

Figure 20C:
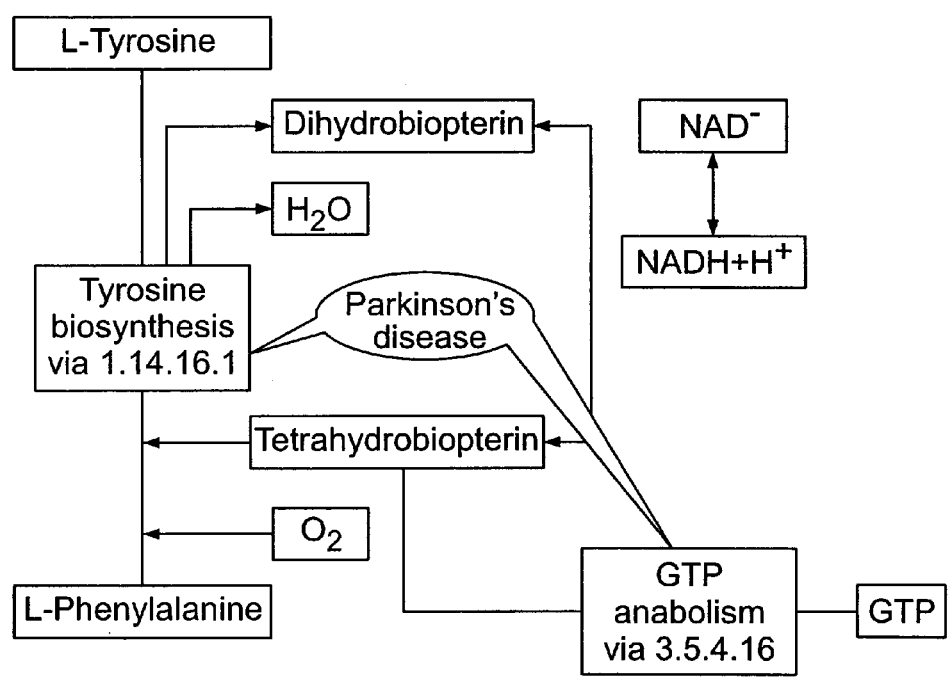
FIG. 20C is an illustration showing an enlarged view of a portion of the TCA cycle map in FIG. 20A.

The user interface of the reconstruction is an interactive map (FIG. 20A-C) showing pathways involved in amino acid metabolism. Pathways are interconnected into a network by shared metabolites. By clicking the mouse on a pathway or a component of a pathway, a user can access the pathway page showing detailed diagrams with all reactions and enzymes. In this example, the specific pathway for serine biosynthesis is illustrated. Similar information is available for other areas of metabolism, and the System Reconstruction technology can be applied to any area of metabolism. By clicking on the link for "serine biosynthesis via 3.1.3.3" as shown on the TCA cycle diagram in FIG. 20A, the link to the serine biosynthesis scheme (FIG. 21) is accessed. While serine biosynthesis is used as an example here, the database contains similar integrated information for each pathway or component that has a dot in the corner, as seen in FIG. 20A-C.

Figure 21:
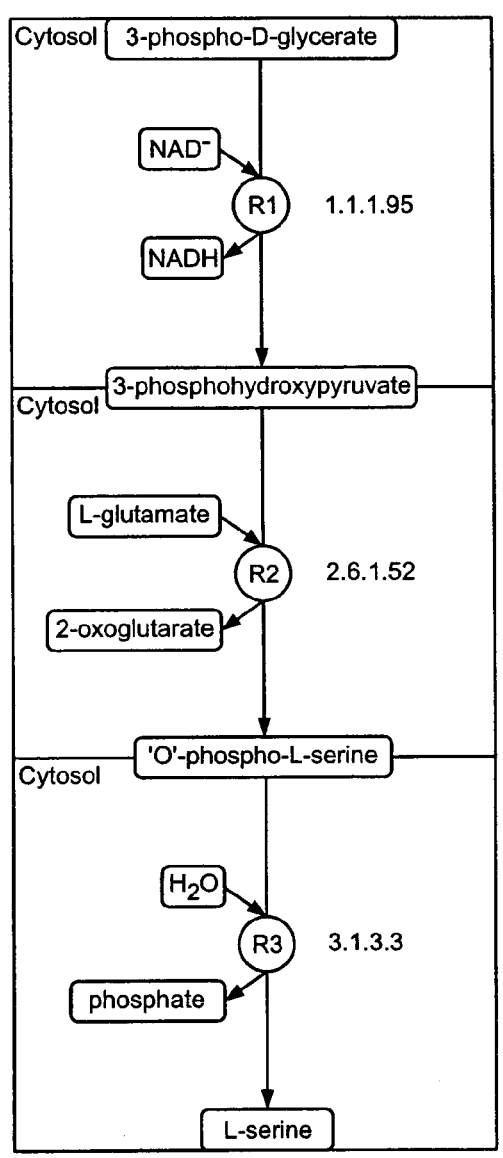
FIG. 21 illustrates a serine biosynthesis scheme (3-phospho-D-glycerate/L-glutamate//2-oxoglutarate/L-serine//cyt).
Figure 32A:
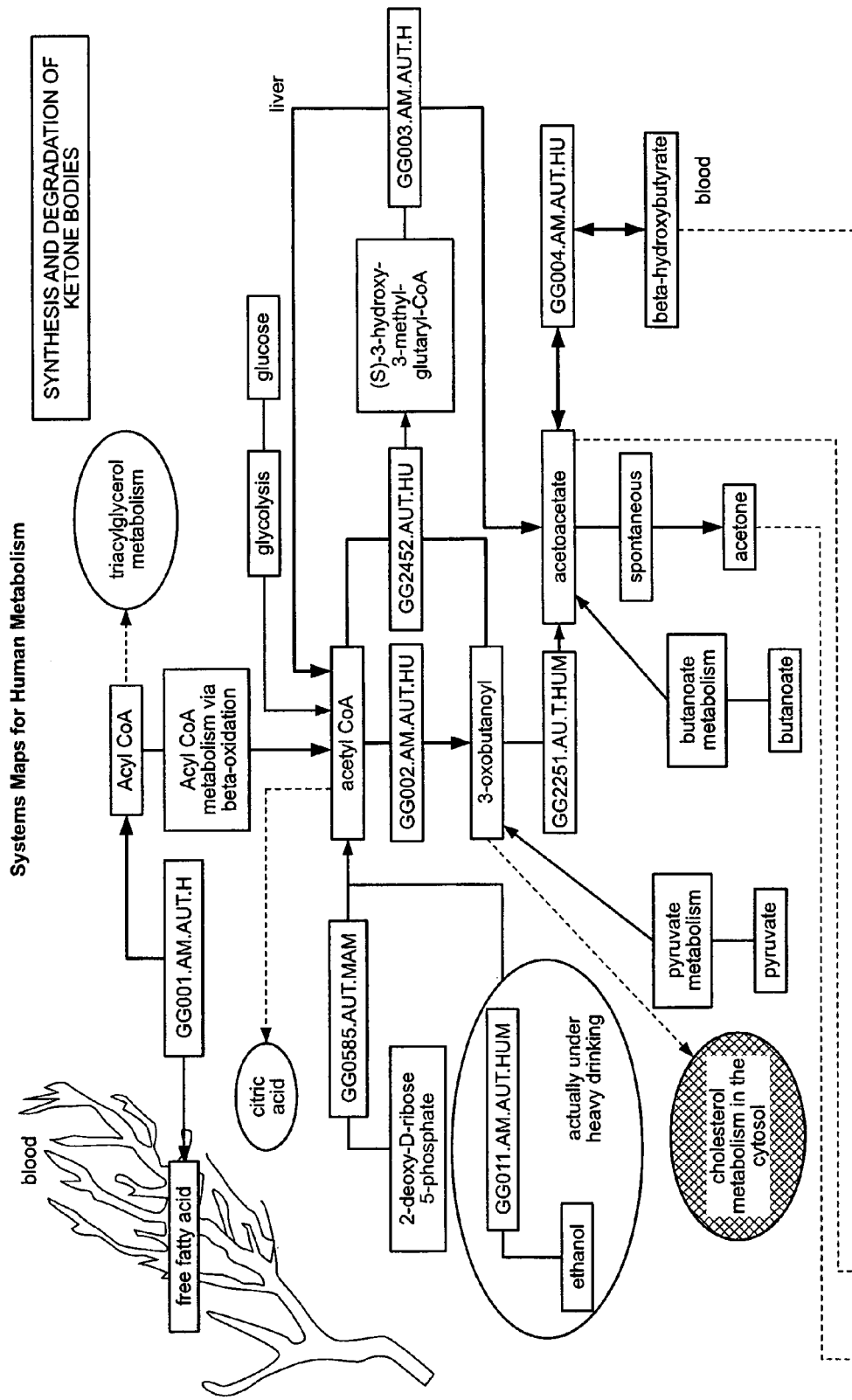
FIG. 32A is a schematic diagram of Systems Maps for Human Metabolism.
Figure 32B:
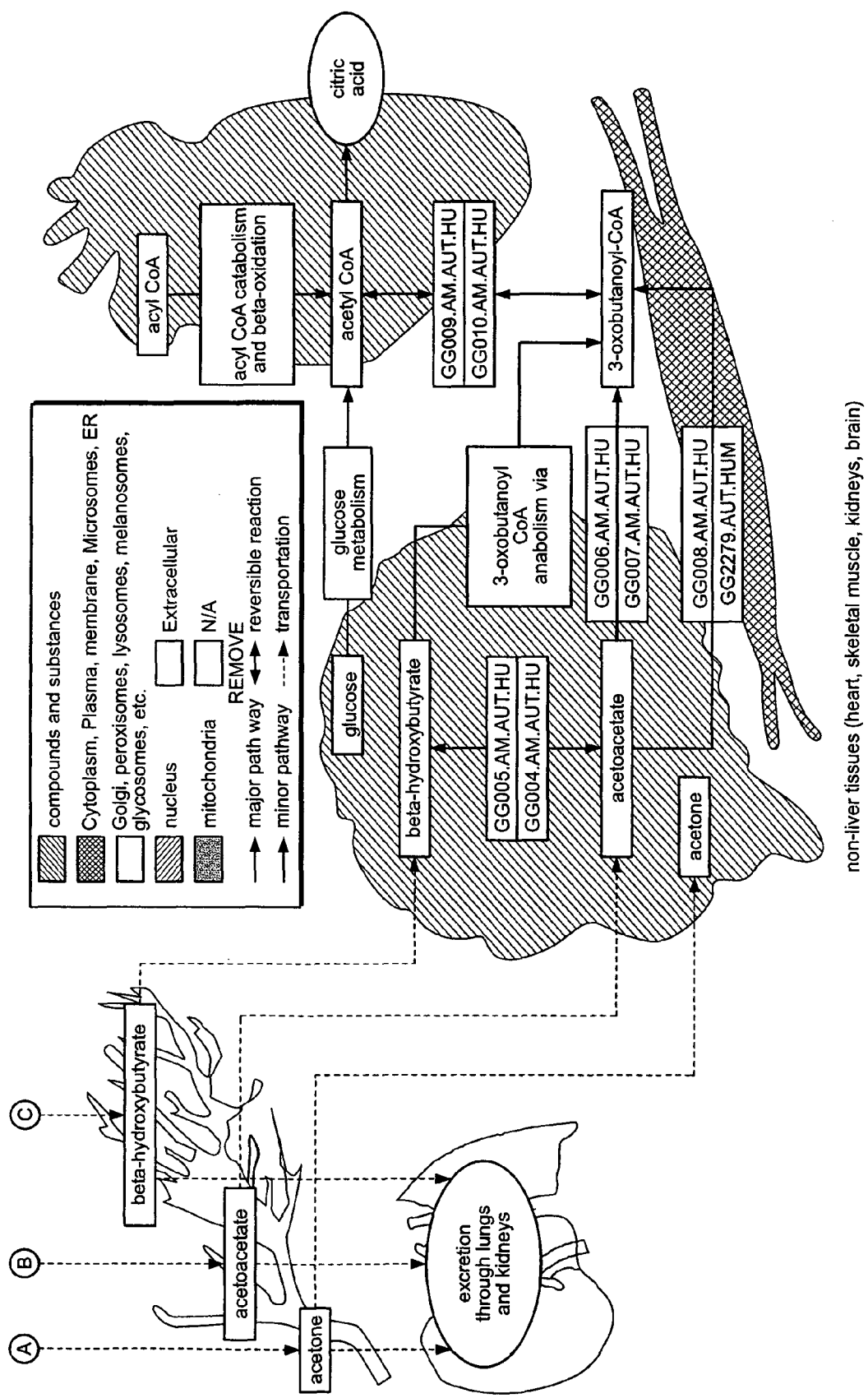
FIG. 32B is a schematic diagram of Systems Maps for Human Metabolism continued from FIG. 32A.
Figure 33A:
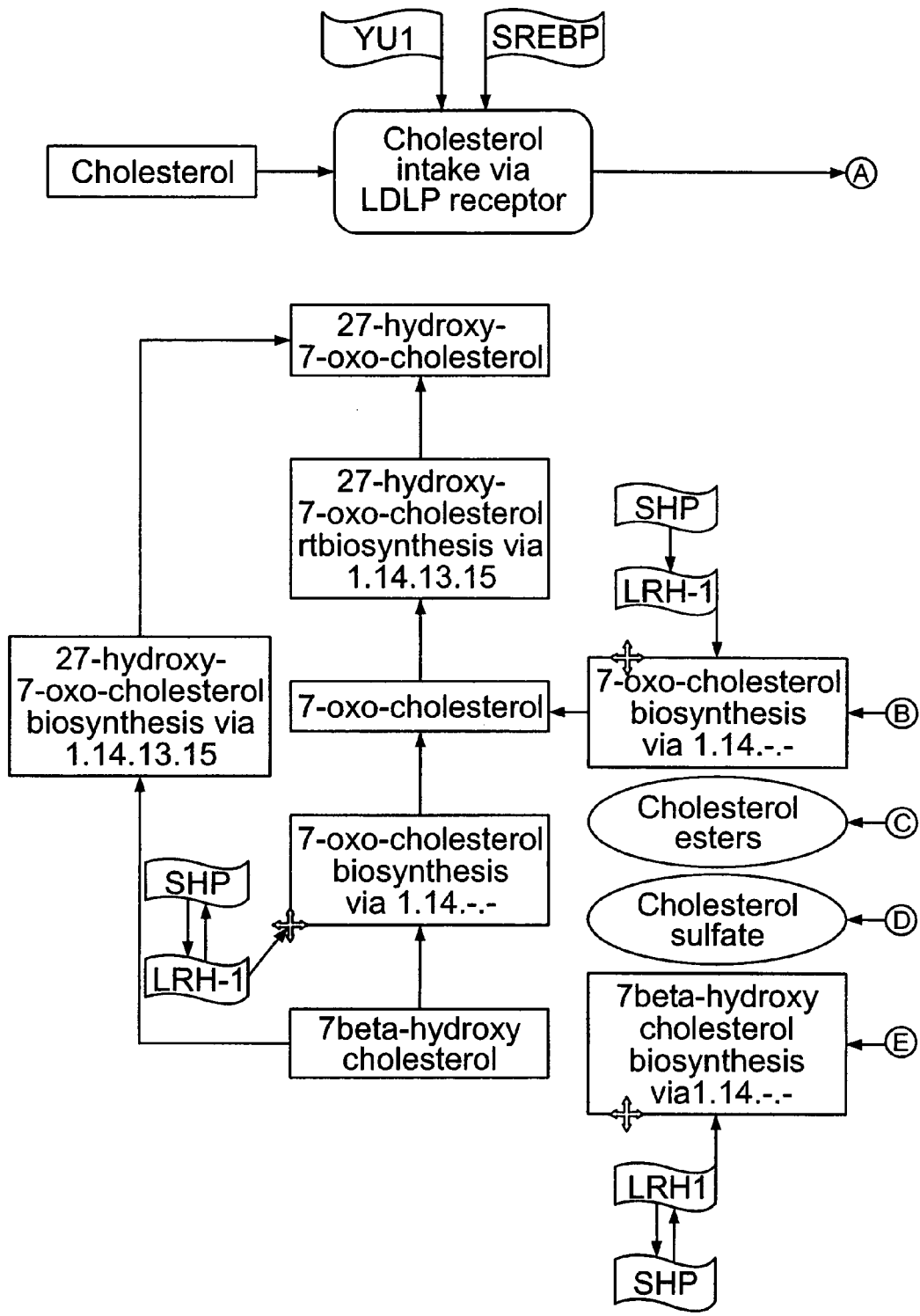
FIG. 33A is a schematic diagram of Systems Maps for Regulation.
Figure 33B:
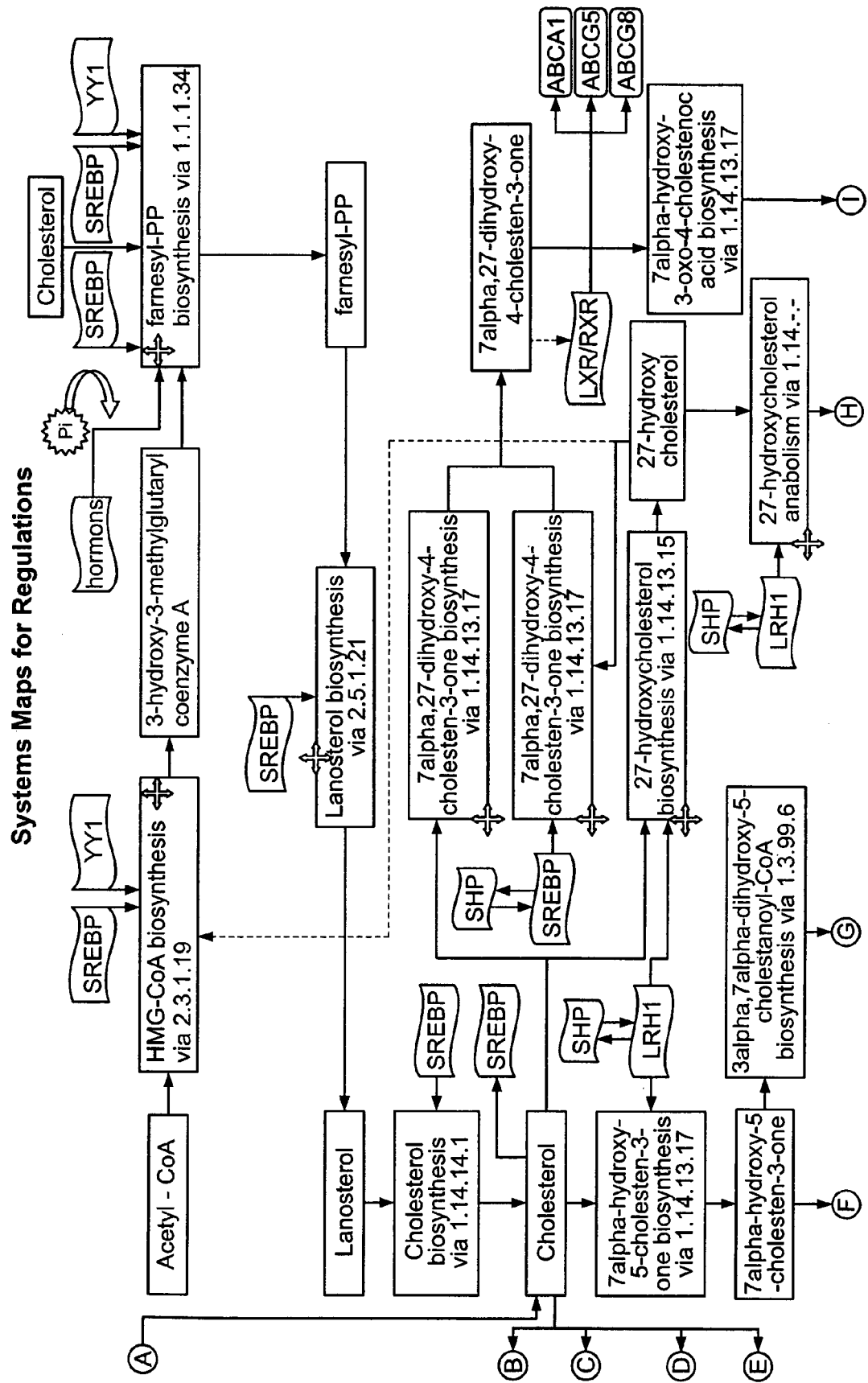
FIG. 33B is a schematic diagram of Systems Maps for Regulation continued from FIG. 33A.
Figure 33C:
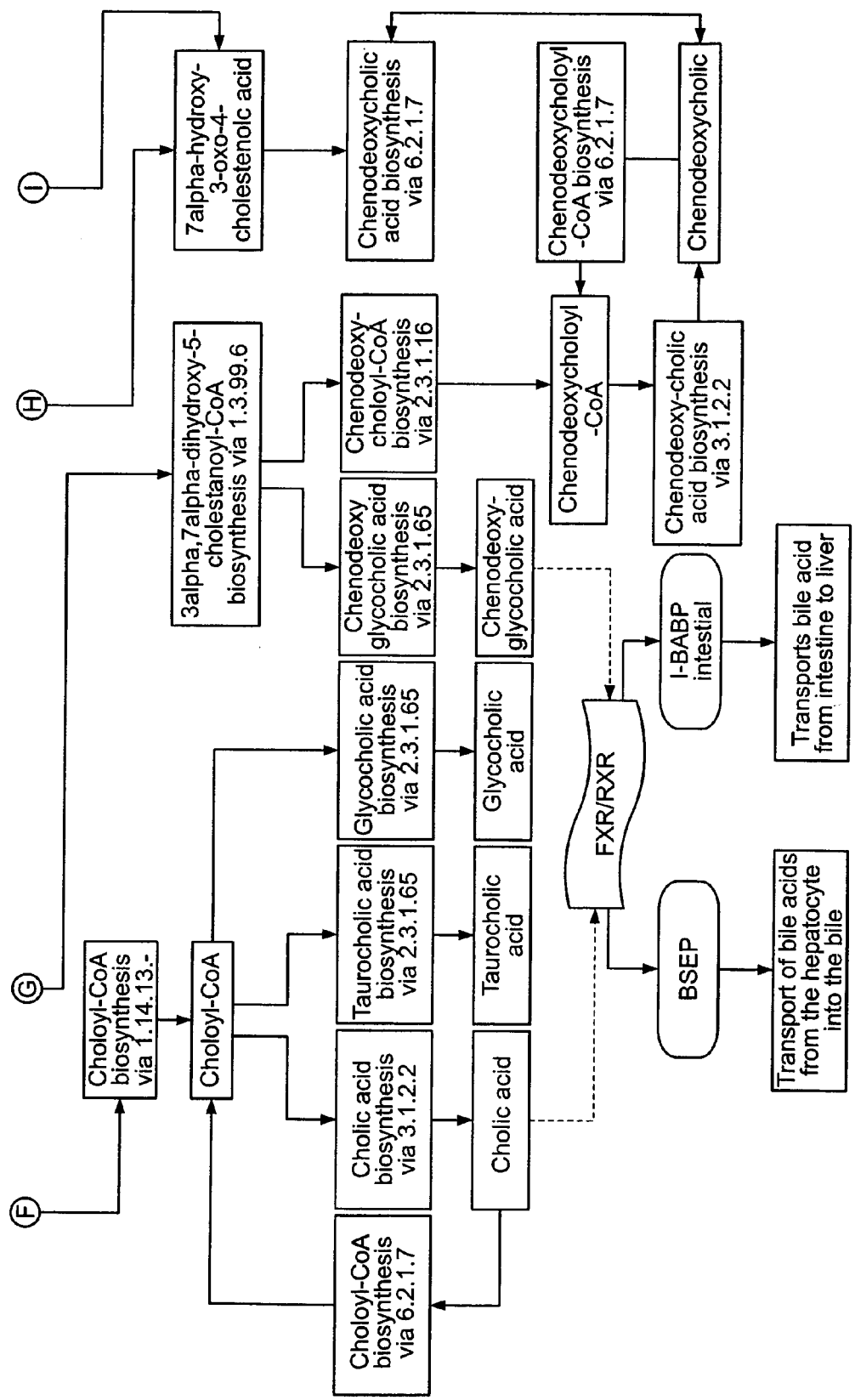
FIG. 33C is a schematic diagram of Systems Maps for Regulation continued from FIGS. 33A and 33B.
Figure 34:
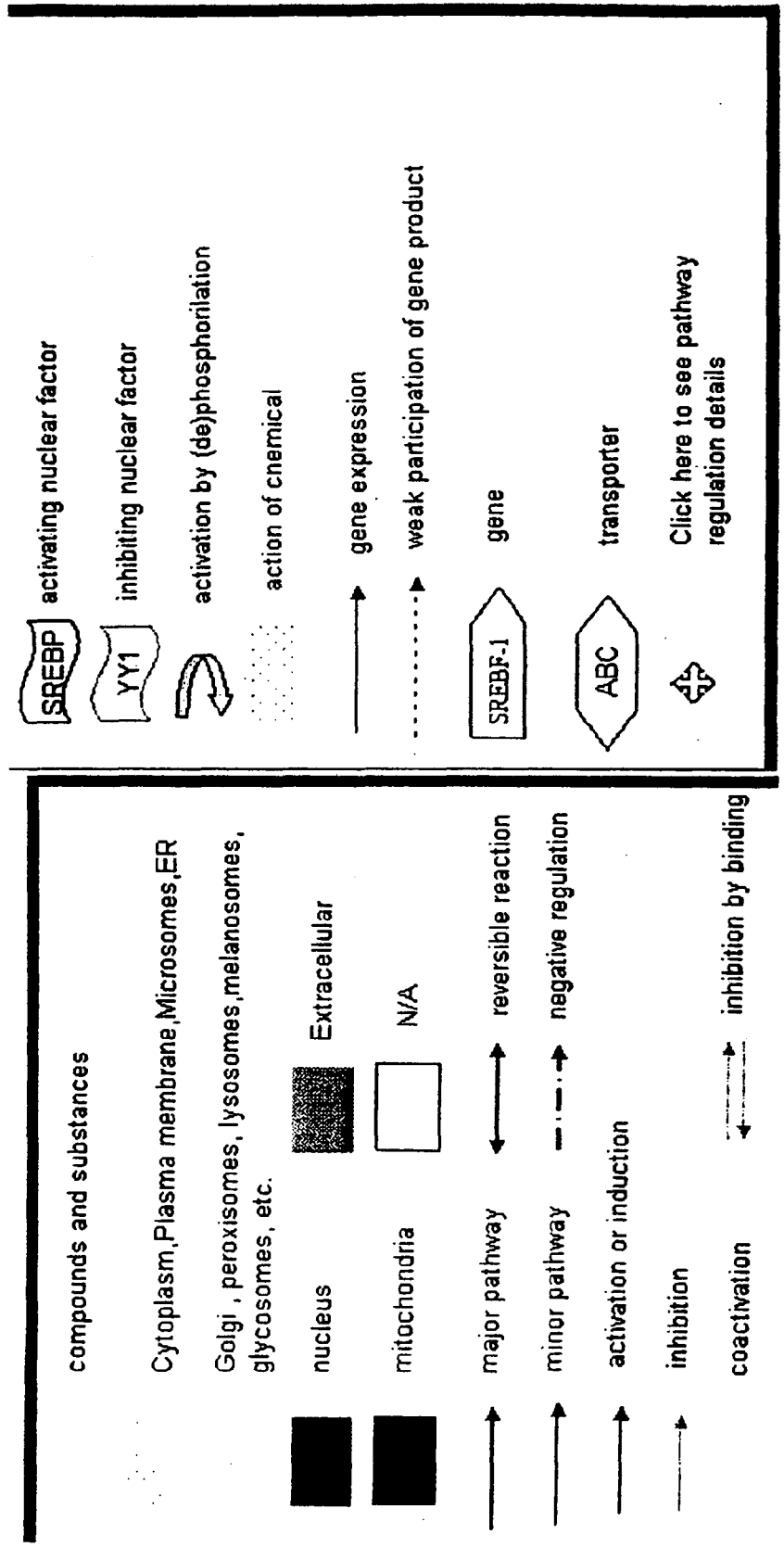
FIG. 34 illustrates a legend of Regulatory Elements.
Figure 35:
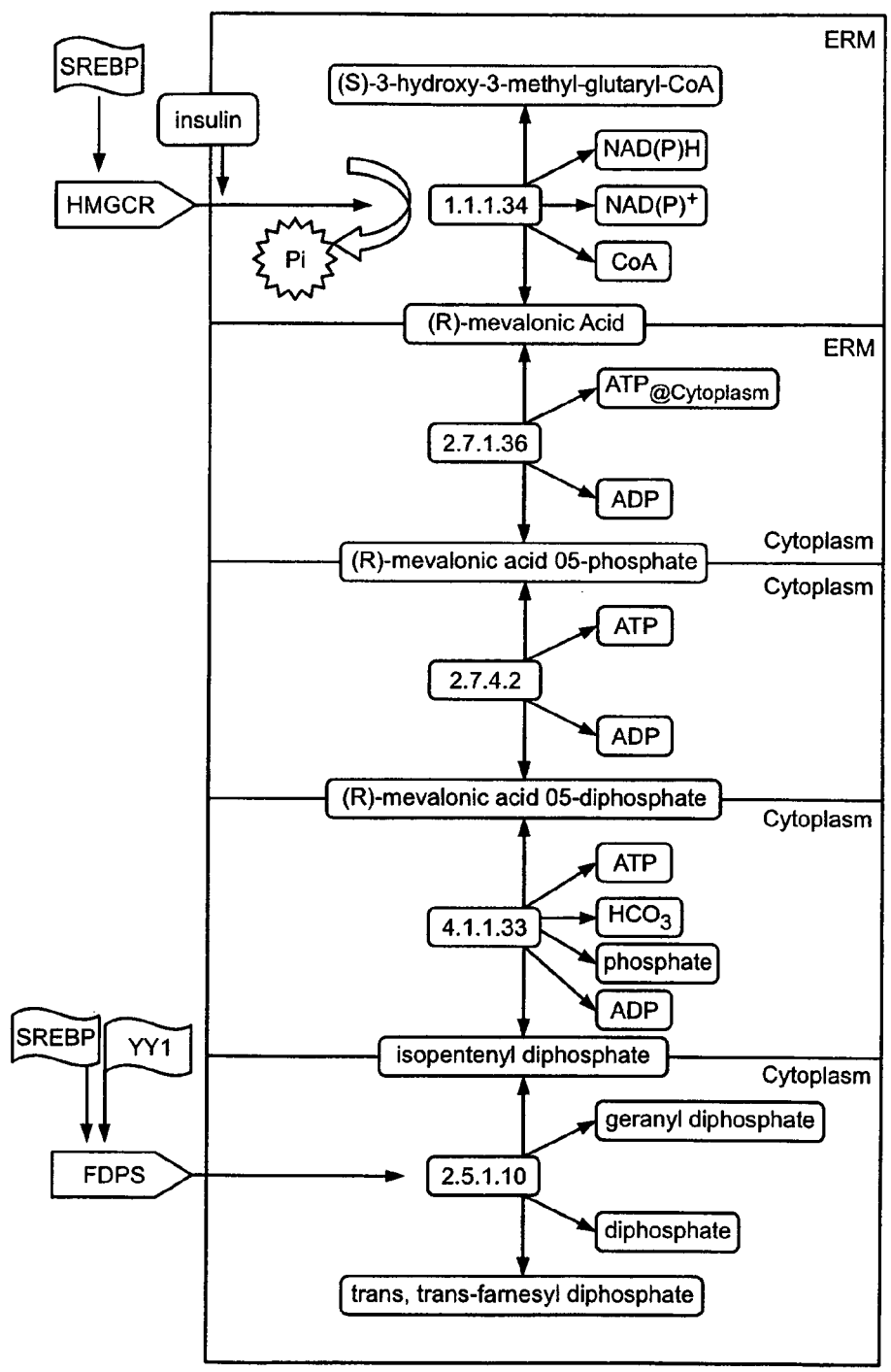
FIG. 35 is a schematic diagram of Links between Metabolism and Regulation.

The serine biosynthesis scheme, illustrated in FIG. 21, shows each reaction of the pathway, each enzyme, and the cellular localization of each reaction. Notes regarding the pathway are accessible from the serine biosynthesis scheme page (FIG. 21) by clicking on "notes." The notes associated with the serine biosynthesis scheme are shown in FIG. 22A-B. The notes page (FIG. 22A-B) contains (1) a list of the reactions involved; (2) the enzymes, including the EC number, the name of the associated gene, expression information, and links to ESTs; (3) annotations including diseases associated with the pathway, information about the diseases, and links to references about the diseases; and (4) a list of tissues and cell types in which the pathway is known to occur.

Details for each reaction in the pathway also are accessible from the scheme page. In the serine biosynthesis scheme (FIG. 21), additional information is accessible by clicking on a reaction center (indicated as R1, R2, or R3 in FIG. 21) or by clicking on an enzyme (indicated as 1.1.1.95, 2.6.1.52, or 3.1.3.3 in FIG. 21). For example, by clicking on R1 in FIG. 21, one can access the reaction page for the first reaction in the pathway (3-phospho-D-glycerate+NAD+=3-phosphohydroxypyruvate+NADH), shown in FIG. 23. The reaction page shows the overall reaction, details of the reaction, the cellular localization of the reaction, the catalyst, and any available annotations.

Form the scheme page (FIG. 21), from the notes page (FIG. 22A-B), or from the reaction page (FIG. 23), various enzyme pages can be accessed. By clicking on 1.1.1.95 from any of these pages, the enzyme page (FIG. 24A-B) for EC 1.1.1.95, phosphoglycerate dehydrogenase, is accessed. The enzyme page (FIG. 24A-B) contains a list of alternative names for the enzyme, genes associated with the enzyme, pathways and reactions in which the enzyme is involved, and annotations regarding the enzyme. Annotations can include, for example, information on diseases associated with the enzyme, tissues and cells in which the disease has been implicated, and links to references. Additional reaction pages are shown for reaction 2 of the serine biosynthesis scheme (FIG. 25) and reaction 3 of the serine biosynthesis scheme (FIG. 27). Additional enzyme pages are shown for the enzymes which catalyze reactions 2 and 3 in FIGS. 26 and 28, respectively.

Links to nucleic acid sequences and related literature are also available from the enzyme pages. For example, from the enzyme page for EC 3.1.3.3, phosphoserine phosphatase, shown in FIG. 28, one can access a gene page (FIG. 29) by clicking on the gene name. In this case, by clicking on PSPH, the user is linked to the gene page for phosphoserine phosphatase, EC 3.1.3.3, as shown in FIG. 29. The gene page contains information including the symbol used for the gene, its chromosomal localization, alternate names, expression data, the amino acid sequence encoded by the gene, and links to ESTs.

Examples of sequences linked to the enzyme page (FIG. 28) or to the gene page (FIG. 29) are shown in FIGS. 30A-B and 31A-C. FIG. 30A-B is the SWISS-PROT page for EC 3.1.3.3, phosphoserine phosphatase, and FIG. 31A-C is UniGene page for EC 3.1.3.3, phosphoserine phosphatase.

EXAMPLE 3

Parkinson's Disease

Figure 15:
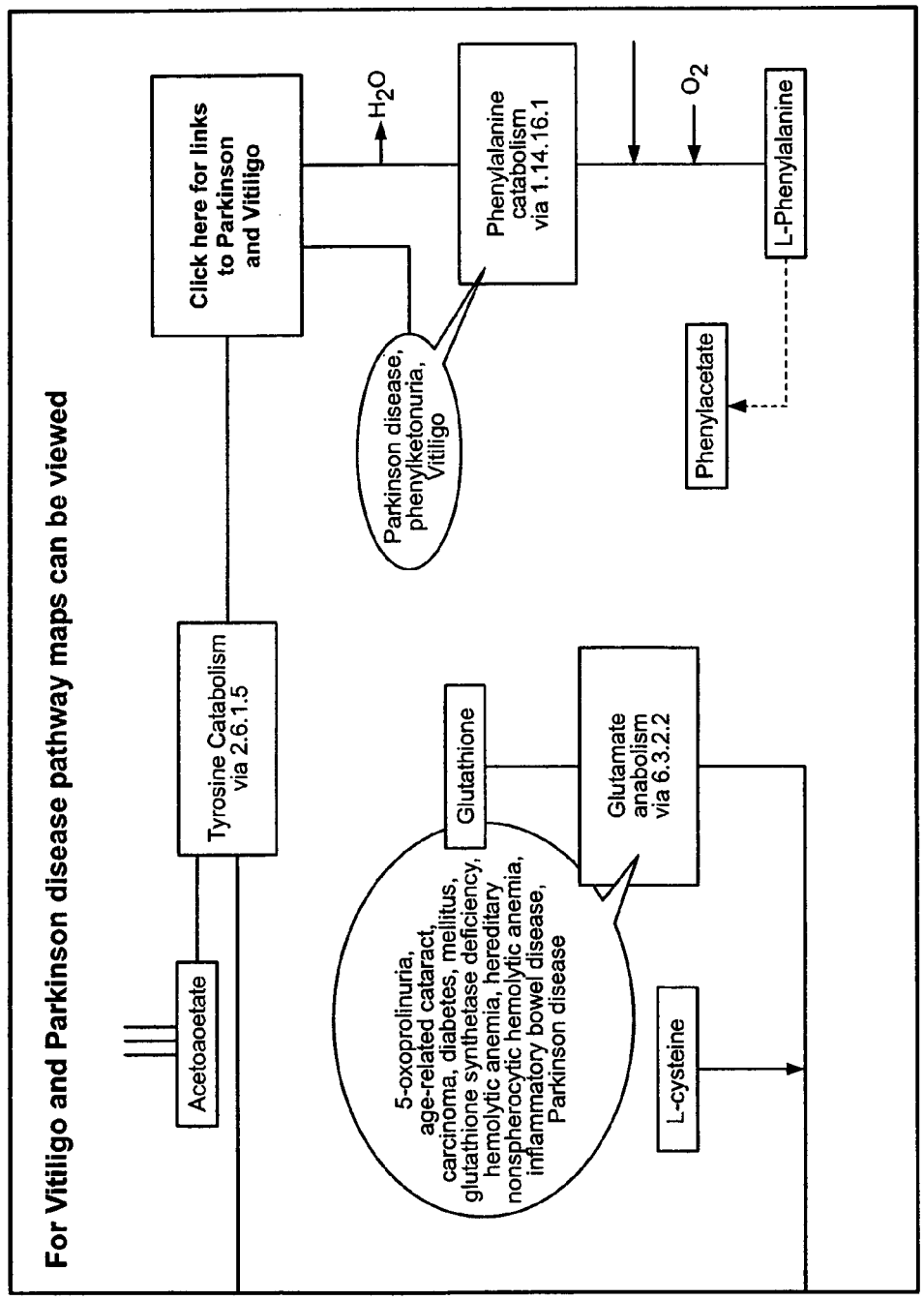
FIG. 15 is an example of a diagram showing diseases associated with pathways, specifically showing links for Vitiligo and Parkinson disease pathway maps.
Figure 16:
FIG. 16 shows a Vitiligo page.

The System Reconstruction method used to analyze amino acid metabolism in humans, as discussed in Example 2, allowed the elucidation of a number of previously unidentified metabolic links. One such example is related to Parkinson's disease. As illustrated in FIG. 15, diseases associated with various enzymes can be indicated on the interactive metabolic map. By clicking in a link for the disease, or a link for diseases known to be associated with a particular enzyme, the user can access additional information about the mechanism of the disease.

Figure 18:
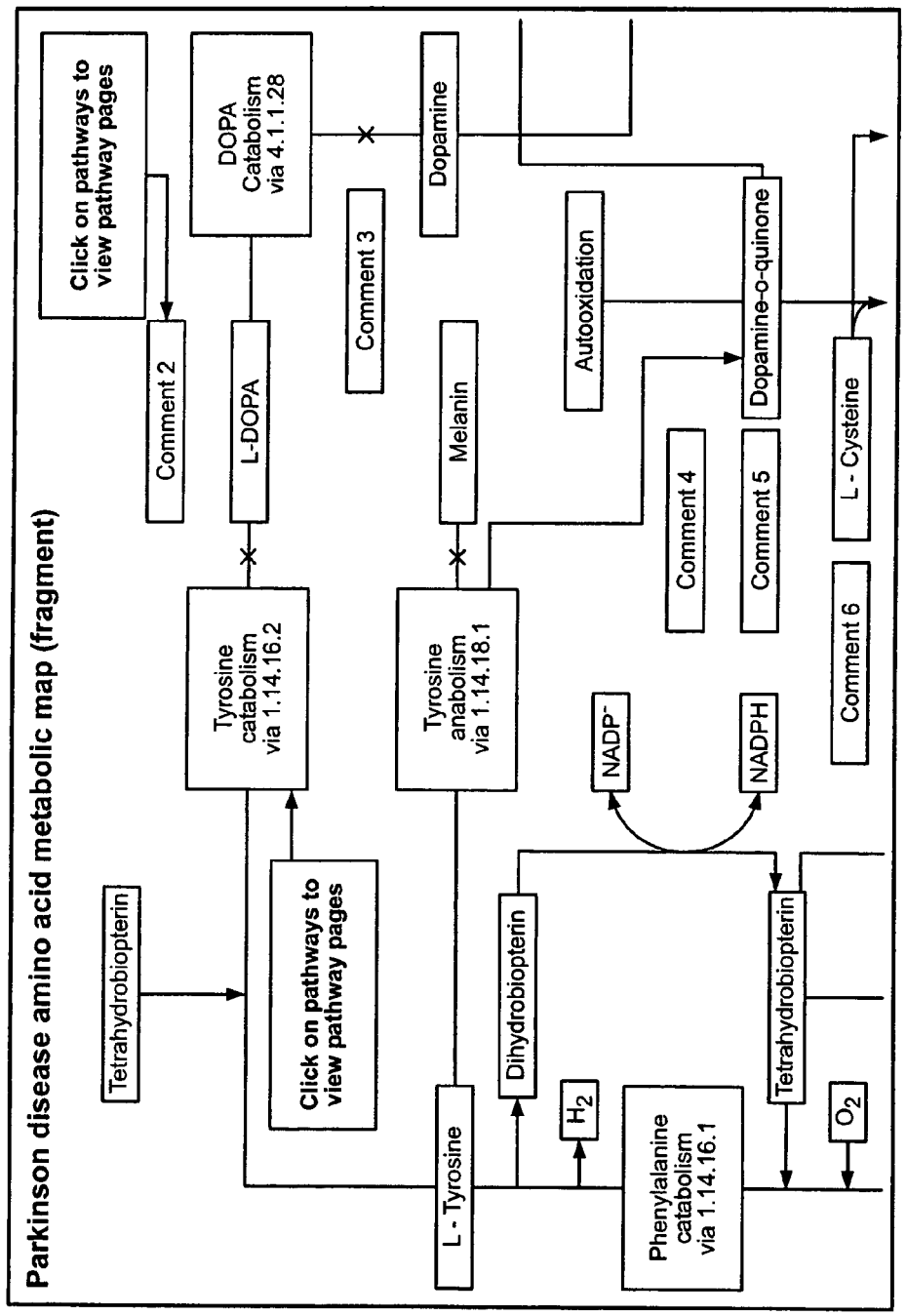
FIG. 18 is an illustration of a Parkinson disease amino acid metabolic map (fragment).
Figure 19:
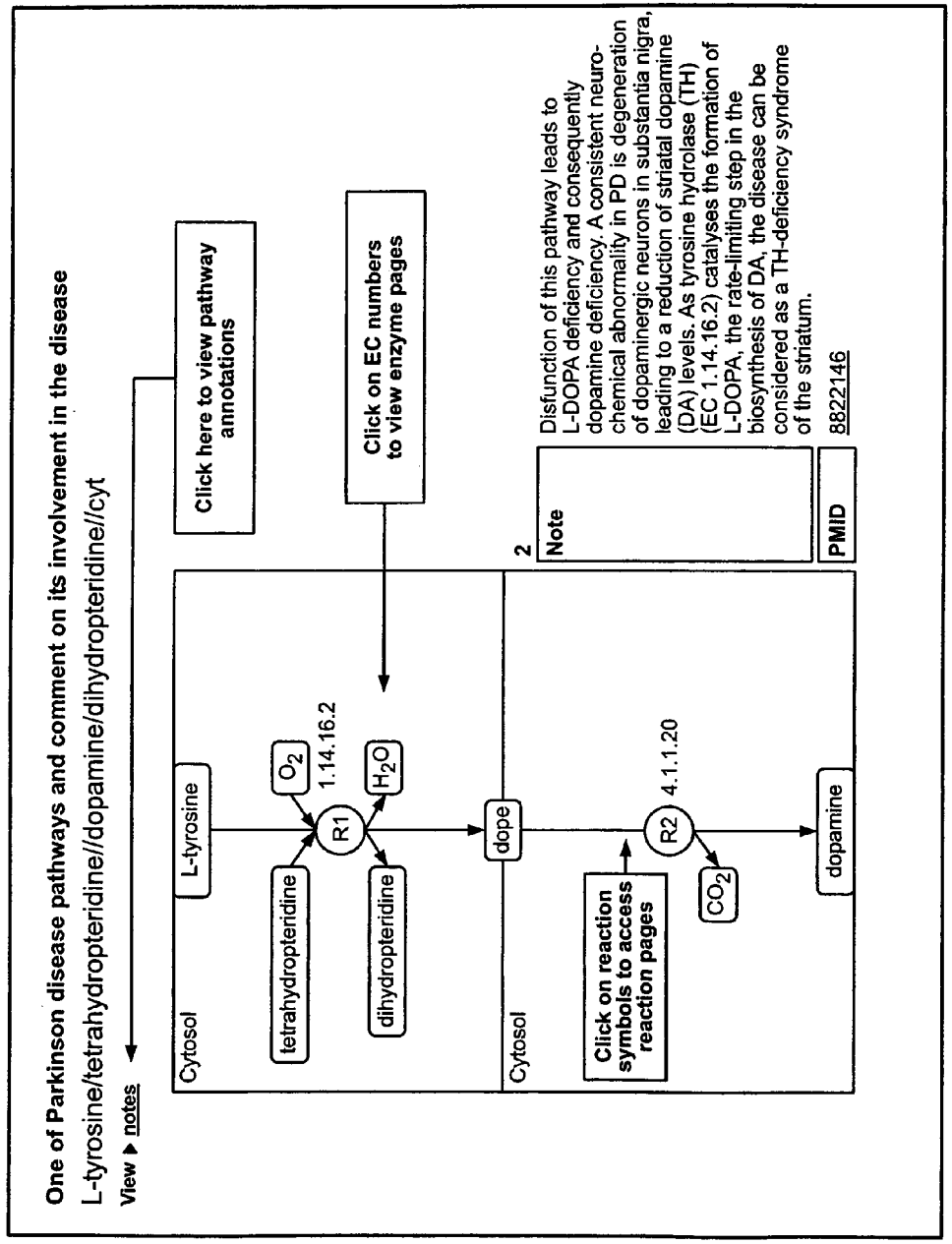
FIG. 19 is an illustration of one of the Parkinson disease pathways and comments.

By clicking on the link for Parkinson's disease from the phenylalanine catabolism portion of the interactive metabolic map (FIG. 15), additional information about Parkinson's disease is accessed. The user is linked to FIG. 17, the Parkinson's disease page. The disease page contains the name of the disease and related diseases or syndromes, and notes regarding the disease, including links to articles relating to the disease. A map of the metabolism specifically associated with the disease is also accessible. FIG. 18 shows a portion of the metabolic pathways that are specifically associated with Parkinson's disease and how those pathways are altered in the disease state. From the disease metabolic map (FIG. 18), the user can access pathway pages and pages with additional comments on the mechanism of the disease. One such disease pathway page is illustrated in FIG. 19.

The metabolic map for Parkinson's disease shows the mechanism by which L-DOPA metabolism is linked to a respiratory pathway (via 1.6.5.3). Deficiencies in L-DOPA metabolism have long been known as one of the causes of Parkinson's disease. The involvement of the respiratory pathway is, however, a recent discovery. This illustrates one example of how of linkages are determined through the method of System Reconstruction.

As illustrated by the foregoing examples, System Reconstruction provides a highly interactive visual overview of metabolism as well as easy access to an abundant amount of information related to the metabolic pathways in question.

Those skilled in the art will readily understand that variations of the materials, conditions, and processes described in these examples can be used. All references cited herein are incorporated by reference.

What is claimed is:

1. A non-transitory computer-readable medium having embodied thereon a set of computer executable instructions configured to enable a computing device to perform a method for reconstructing human metabolism, said method comprising:
   (a) collecting metabolic data;
   (b) linking the data into at least two metabolic pathways using a relational database;
   (c) ranking the metabolic pathways based on their relevance to human metabolism assigning each pathway to one of the following categories, from the most relevant to the least relevant to human metabolism: (i) a multi-step pathway wherein all of the reactions are catalyzed by known human enzymes and/or enzymes that have open reading frame (ORF) candidates in the human genome; (ii) a multi-step pathway wherein only the first and last reactions are catalyzed by known human enzymes and/or enzymes that have ORF candidates in the human genome; (iii) a multi-step pathway wherein only an intermediate reaction is catalyzed by an identified human enzyme or an enzyme that has an ORF candidate in the human genome; and (iv) a multi-step pathway wherein none of the reactions are catalyzed by identified human enzymes or enzymes that has an have ORF candidates in the human genome;
   (d) generating structured annotations of the ranked metabolic pathways;
   (e) identifying interconnections between the ranked and annotated metabolic pathways;
   (f) creating an interactive map of human metabolism on the basis of information obtained in steps (a) through (f).

2. The medium of claim 1, wherein the metabolic data comprises expressed sequence tag data.

3. The medium of claim 1, wherein the linking of data into metabolic pathways is based at least in part on shared inputs and outputs of the pathways.

4. The medium of claim 1, wherein the metabolic data comprises heterogeneous biological data.

5. The medium of claim 4, wherein the metabolic data further comprises expressed sequence tag data.

6. The medium of claim 4, wherein said heterogeneous biological data comprises biochemical units comprising metabolic steps, chemical compounds, reactions and/or enzymatic functions.

7. The medium of claim 6, wherein said enzymatic functions comprise genes and proteins.

8. The medium of claim 6, wherein each of said biochemical units is linked to an annotation table, said annotation table comprising at least one field.

9. The medium of claim 8, wherein said at least one field is selected from the group consisting of organ localization, tissue localization, intracellular localization, intracellular compartmentalization, subcellular localization in another organism, a relationship to a disease, and a reference to an information source.

10. The medium of claim 1, wherein the generation of structured annotations of the ranked metabolic pathways comprises:
    (a) comparing the ranked metabolic pathways to published information;
    (b) confirming, modifying or rejecting the ranked metabolic pathways based on their differences from the published information; and
    (c) describing the ranked pathways as a hierarchy of biochemical units.

11. The medium of claim 10, wherein the biochemical units comprise a ranked metabolic pathway, metabolic steps that constitute the pathway, chemical compounds, reactions and/or enzymatic functions.

12. The medium of claim 11, wherein said enzymatic functions comprise genes and proteins.

13. The medium of claim 11, wherein each of said biochemical units is linked to an annotation table.

14. The medium of claim 13, wherein said annotation table comprises at least one field selected from the group consisting of organ localization, tissue localization, intracellular localization, intracellular compartmentalization, subcellular localization in another organism, a relationship to a disease, and a reference to an information source.

15. A non-transitory computer-readable medium having embodied thereon a set of computer executable instructions that perform a method for identifying a human drug target, said method comprising:
    (a) collecting data for both non-disease and disease states;
    (b) linking the data into at least two metabolic pathways using a relational database;
    (c) ranking the metabolic pathways based on their relevance to human metabolism assigning each pathway to one of the following categories, from the most relevant to the least relevant to human metabolism: (i) a multi-step pathway wherein all of the reactions are catalyzed by known human enzymes and/or enzymes that have open reading frame (ORF) candidates in the human genome; (ii) a multi-step pathway wherein only the first and last reactions are catalyzed by known human enzymes and/or enzymes that have ORF candidates in the human genome; (iii) a multi-step pathway wherein only an intermediate reaction is catalyzed by an identified human enzyme or an enzyme that has an ORF candidate in the human genome; and (iv) a multi-step pathway wherein none of the reactions are catalyzed by identified human enzymes or enzymes that has an have ORF candidates in the human genome;
    (d) generating structured annotations of the ranked metabolic pathways;
    (e) identifying interconnections between the ranked and annotated metabolic pathways;
    (f) creating an interactive map of human metabolism on the basis of information obtained in steps (a) through (f); and
    (g) identifying a human drug target by comparing differences between non-disease and disease states using the interactive map.

16. A non-transitory computer-readable medium having embodied thereon a set of computer executable instructions that perform a method for identifying a target for human gene therapy, said method comprising:
    (a) collecting data for a first developmental state and a second developmental state;
    (b) linking the data into at least two metabolic pathways using a relational database;
    (c) ranking the metabolic pathways based on their relevance to human metabolism assigning each pathway to one of the following categories, from the most relevant to the least relevant to human metabolism: (i) a multi-step pathway wherein all of the reactions are catalyzed by known human enzymes and/or enzymes that have open reading frame (ORF) candidates in the human genome; (ii) a multi-step pathway wherein only the first and last reactions are catalyzed by known human enzymes and/or enzymes that have ORF candidates in the human genome; (iii) a multi-step pathway wherein only an intermediate reaction is catalyzed by an identified human enzyme or an enzyme that has an ORF candidate in the human genome; and (iv) a multi-step pathway wherein none of the reactions are catalyzed by identified human enzymes or enzymes that has an have ORF candidates in the human genome;

(d) generating structured annotations of the ranked metabolic pathways;

(e) identifying interconnections between the ranked and annotated metabolic pathways;

(f) creating an interactive map of human metabolism on the basis of information obtained in steps (a) through (f);

(g) identifying a target for human gene therapy by comparing differences between the first developmental state and the second developmental state using the interactive map.

17. A non-transitory computer-readable medium having embodied thereon a set of computer executable instructions that perform a method for identifying interconnections between human biological processes, said method comprising:

(a) collecting data of at least two biological processes, said data comprising inputs and outputs of the processes;

(b) linking the data into at least two pathways based on shared inputs and outputs using a relational database;

(c) ranking the pathways based on their relevance to the human biological processes assigning each pathway to one of the following categories, from the most relevant to the least relevant to the human biological process: (i) a multi-step pathway wherein all of the reactions are catalyzed by known human enzymes and/or enzymes that have open reading frame (ORF) candidates in the human genome; (ii) a multi-step pathway wherein only the first and last reactions are catalyzed by known human enzymes and/or enzymes that have ORF candidates in the human genome; (iii) a multi-step pathway wherein only an intermediate reaction is catalyzed by an identified human enzyme or an enzyme that has an ORF candidate in the human genome; and (iv) a multi-step pathway wherein none of the reactions are catalyzed by identified human enzymes or enzymes that has an have ORF candidates in the human genome;

(d) generating structured annotations of the ranked pathways;

(e) identifying interconnections between the ranked and annotated pathways;

(f) creating an interactive map of the human biological processes on the basis of information obtained in steps (a) through (f).

* * * * *